US007300774B1

(12) United States Patent
Kornbluth

(10) Patent No.: US 7,300,774 B1
(45) Date of Patent: *Nov. 27, 2007

(54) MULTIMERIC FUSION PROTEINS OF THE TNF SUPERFAMILY LIGANDS

(75) Inventor: Richard S. Kornbluth, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/454,223

(22) Filed: Dec. 9, 1999

(51) Int. Cl.
*C12P 21/02* (2006.01)
*C07K 14/525* (2006.01)

(52) U.S. Cl. .................................. 435/69.5; 530/351
(58) Field of Classification Search ............. 530/387.5, 530/350, 395
See application file for complete search history.

(56) References Cited

U.S. PATENT DOCUMENTS

| | | | |
|---|---|---|---|
| 5,716,805 A | 2/1998 | Srinivasan et al. | 435/69.1 |
| 5,962,406 A | 10/1999 | Armitage et al. | 514/8 |
| 6,017,527 A * | 1/2000 | Maraskovsky et al. | 424/93.71 |
| 6,018,026 A | 1/2000 | Sledziewski et al. | 530/350 |
| 6,190,886 B1 | 2/2001 | Hoppe et al. | 435/69.7 |
| 2003/0053894 A1 | 3/2003 | Tschopp et al. | 424/85.1 |
| 2004/0047873 A1 | 3/2004 | Al-Shamkhani et al. | 424/185.1 |
| 2004/0248801 A1 | 12/2004 | Kiessling et al. | 514/12 |

FOREIGN PATENT DOCUMENTS

| | | |
|---|---|---|
| WO | WO 93/08207 | 4/1993 |
| WO | WO 94/10308 | 5/1994 |
| WO | WO 99/04000 | 1/1999 |
| WO | WO 01/16180 | 3/2001 |
| WO | WO 01/49866 | 7/2001 |
| WO | WO 03/068799 | 8/2003 |

OTHER PUBLICATIONS

Stone et al. Multimeric soluble CD40 ligand and GITR ligand as adjuvants for human immunodeficiency virus DNA vaccines (2006), J. of Virol., vol. 80, pp. 1762-1772.*
Tamada et al. Renewed interest in cancer immunotherapy with the tumor necrosis factor superfamil molecules (2006), Can. Imm. immunother., vol. 55, pp. 355-362.*
Bodmer et al., Trends Biochem. Sci. 27:19-26.*
Kornbluth, J Hematother Stem Cell Res. Oct. 2002;11(5):787-801, Abstract Only.*
Schoenberger et al., Nature. Jun. 4, 1998;393(6684):480-3., Abstract Only.*
Hoppe et al., FEBS Lett. May 16, 1994;344(2-3):191-5.*
Morris et al., "Incorporation of an Isoleucine Zipper Motif Enhances the Biological Activity of Soluble CD40L (CD154)", The Journal of Biological Chemistry, vol. 274, No. 1, pp. 418-423, (1999).

Holler et al., "Two Adjacent Trimeric Fas Ligands Are Required for Fas Signaling and Formation of a Death-Inducing Signaling Complex", Molecular and Cellular Biology, vol. 23, No. 4 (2003).
Haswell et al., "Analysis of the Oligomeric Requirement for Signalling by CD40 using Soluble Multimeric Forms of Its Ligand, CD154", Eur. J. Immunol., vol. 31:3094-3100 (2001).
Haswell et al., "Analysis of the oligomeric requirement for signaling by CD40 using multimeric forms of its ligand, CD154", *Eur. J. Immunol*, vol. 31, pp. 3094-3100, (2001).
Hoppe et al., "A parallel three stranded γ-helical bundle at the nucleation site of collagen triple-helix formation", *FEBS Letters*, vol. 344, pp. 191-195, (1994).
Kishore et al., "Modular organization of proteins containing C1q-like globular domain", *Immunopharmacology*, vol. 42, pp. 15-21, (1999).
Kornbluth et al., "CD40L (CD154) fusion protein with pulmonary surfactant protein D as a prototype for soluble multimeric TNF superfamily ligand molecules", *FASEB Journal*, vol. 14, No. 6, A1162, (2000).
Pound et al., "Minimal cross-linking and epitope requirements for CD40-dependent suppression of apoptosis contrast with those promotion of the cell cycle and homotypic adhesion in human B cells", *International Immunology*, vol. 11, No. 1, pp. 11-20, (1999).
Sano et al., "Analysis of Chimeric Proteins Identifies the Regions in the Carbohydrate Recognition Domains of Rat Lung Collectins That Are Essential for Interactions with Phospholipids, Glycolipids, and Alveolar Type II Cells", *J. Biol. Chem*, vol. 273, No. 8, pp. 4783-4789, (1998).
Schneider et al, "Conversion of Membrane-bound Fas (CD95) Ligand to Its Soluble Form Is Associated with Downregulation of Its Proapoptotic Activity and Loss of Liver Toxicity", *J. Exp. Med.*, vol. 187, No. 8, pp. 1205-1213, (1998).

* cited by examiner

*Primary Examiner*—Gary B. Nickol
*Assistant Examiner*—Cherie Woodward
(74) *Attorney, Agent, or Firm*—DLA Piper US LLP

(57) ABSTRACT

A method for constructing stable bioactive fusion proteins of the difficult to express tumor necrosis factor superfamily (TNFSF), and particularly members CD40L (CD154) and RANKL/TRANCE, with collecting, particularly pulmonary surfactant protein D (SPD) is described. Single trimers of these proteins lack the full stimulatory efficacy of the natural membrane forms of these proteins in many cases. The multimeric nature of these soluble fusion proteins enables them to engage multiple receptors on the responding cells, thereby, mimicking the effects of the membrane forms of these ligands. For CD40L-SPD, the resulting protein stimulates B cells, macrophages, and dendritic cells, indicating its potential usefulness as a vaccine adjuvant. The large size of these fusion proteins makes them less likely to diffuse into the circulation, thereby limiting their potential systemic toxicity. This property may be especially useful when these proteins are injected locally as a vaccine adjuvant or tumor immunotherapy agent to prevent them from diffusing away. In addition, these and other TNFSF-collectin fusion proteins present new possibilities for the expression of highly active, multimeric, soluble TNFSF members.

14 Claims, 7 Drawing Sheets

US 7,300,774 B1

MULTIMERIC FUSION PROTEINS OF THE TNF SUPERFAMILY LIGANDS

GRANT INFORMATION

This invention was made with government support under Grant Nos. AI35258 and HL57911 awarded by the National Institutes of Health. The United States government has certain rights in this invention.

BACKGROUND OF THE INVENTION

1. Field of the Invention

The present invention relates to a method form preparing soluble multimeric proteins consisting of more than three iterations of the same bioactive molecule using recombinant DNA technology.

The present invention particularly concerns a new method of producing multimeric fusion proteins involving the TNF superfamily (TNFSF) members as a fusion proteins with SPD, and more specifically, CD40L-SPD fusion proteins and useful modifications thereof.

2. Description of Related Art

Numerous proteins can be made using modern molecular biology techniques and used in diagnostic and therapeutic applications. Using recombinant DNA techniques, the DNA encoding a single amino acid chain is constructed and then introduced into a cell which manufactures the final protein. Some cells, especially bacteria like *E. coli*, lack the ability to properly fold the amino acid chains into the proper quaternary structure and they often fail to apply the necessary modifications (e.g., glycosylation and disulfide bond formation) that are needed for the protein to be bioactive and resistant to degradation in vivo. While most of these challenges can be met by expressing the amino acid chain in eukaryotic cells like yeast or mammalian cells in vitro, it is not always straightforward to express proteins that consist of two or more amino acid chains. In general, for multichain proteins, the single amino acid chains must associate together in some way either within the producer cell or subsequently after the monomers are secreted from the producer cell. For artificially constructed molecules, the introduction into a single amino acid chain of an amino acid sequence which causes this chain-to-chain association can be an important step in producing multichain proteins.

One of the most widely used methods of causing two amino acid chains to associate is to conjoin, at the DNA coding level, segments from the protein of interest and a segment from a spontaneously dimerizing protein. The best example is to conjoin or fuse a protein with the Fc portion of immunoglobulin, creating a dimeric Fc fusion protein (Fanslow et al., *J. Immunol.* 136:4099, 1986). A protein of this type can be formed from the extracellular domain of a tumor necrosis factor (TNF) receptor fused to Fc (termed etanercept and marketed as ENBREL®), which is effective in the treatment of rheumatoid arthritis. A second example is the construction of a fusion protein between the dimerizing extracellular portion of CD8 with the extracellular portion of CD40L (Hollenbaugh et al., *EMBO J.* 11:4313, 1992). Here, the dimerizing CD8 portion of the fusion protein helps to maintain the CD40L portion in the trimeric form needed for its bioactivity. A more recent example is the addition of an isoleucine zipper motif to CD40L, which permits the production of trimeric soluble CD40L molecules (Morris et al., *J. Biol. Chem.* 274:418, 1999).

The TNF superfamily (TNFSF) consists of an expanding number of proteins (see Table I) which are crucial for the development and functioning of the immune, hematological, and skeletal systems. TNFSF proteins are ligands for a corresponding set of receptors of the TNF receptor superfamily (TNFRSF). All TNFSF members are expressed as Type II membrane proteins, with the exception of lymphotoxin-alpha which is produced as a secreted protein. However, soluble forms of several TNFSF proteins can be released from the cell surface by proteolytic cleavage, usually by specific metalloproteinases.

The production of soluble forms of TNFSF proteins has been an important step in the study of these proteins. Soluble TNFSF ligands can be used to study the activities of these proteins in vitro without the complexities in interpretation that result when cells or cellular membranes expressing TNFSF proteins are added. In addition, soluble forms of several TNFSF proteins have potential as therapeutic agents for human diseases. In particular, TNF-? has been extensively studied for the treatment of cancer and soluble CD40L is currently undergoing clinical trials to assess its antitumor effects.

To produce soluble forms of TNFSF proteins, either the membrane protein is expressed in a cell line possessing a protease capable of separating the TNFSF extracellular domain from the transmembrane domain or a truncated form of the TNFSF protein is produced which consists solely of the extracellular domain plus a signal sequence. In either case, certain soluble forms of TNFSF proteins are unstable in solution as simple homotrimers composed solely of the extracellular domain. For example, naturally solubilized TNF-? is labile under physiological conditions [Schuchmann, 1995 #129]. To solve this stability problem, chimeric proteins have been constructed according to one of four different design principles: (1) The extracellular portion of the TNFSF protein has been expressed fused to the dimeric portion of the immunoglobulin Fc fragment U.S. Pat. No. 5,155,027, Oct. 13, 1992, issued to, Andrzej Z. Sledziewski, et al. In the case of CD40L and OX40L, this yields a soluble molecule which is significantly less active than the native membrane form of this protein. (2) The extracellular portion of the TNFSF protein has been expressed with an antigenic tag (usually the FLAG motif) fused to its N-terminus [Mariani, 1996]. The addition of an antibody to the tag (e.g., anti-FLAG antibody) aggregates these proteins into a multimeric form. Crosslinking enhances activity on B cells. (3) The extracellular portion of the TNFSF protein has been expressed fused to the spontaneously dimerizing extracellular portion of the CD8 molecule [Hollenbaugh, 1992]. In the case of CD40L, this creates a hexameric molecule [Pullen, 1999] which is likely formed by two CD40L trimers attached to three CD8 dimeric stalks. Despite this, the addition of an anti-CD8 antibody to crosslink the CD40L-CD8 fusion protein yields a further enhancement of CD40L activity on B cells. (4) The extracellular portion of the TNFSF protein has been expressed fused to a trimerizing isoleucine zipper which maintains the overall trimeric structure of the protein [U.S. Pat. No. 5,716,805, Feb. 10, 1998, issued to Subashini Srinivasan et al. This soluble CD40L trimer or 'sCD40LT' is the form of that protein now being clinically tested in humans for its anti-tumor effects.

Compounding the difficulties in producing stable forms of soluble TNFSF proteins are compromises in bioactivity. As exemplified by FasL, TNF, and CD40L, many of the soluble forms of these proteins lack the full range of stimulatory activities displayed by the membrane forms of these molecules. For FasL, several groups have reported that naturally produced soluble FasL (generated by proteolytic cleavage from the membrane form) has a spectrum of activities that is distinctly different from the membrane form. Soluble FasL induces apoptosis in activated CD4+ T cells but not fresh, resting CD4+ T cells. In contrast, both types of CD4+ T cells are killed by membrane FasL or a recombinant soluble form of FasL (WX1) that spontaneously aggregates into oligomers larger than a decamer. For TNF, T cell activation through stimulation of TNFR II, the 80 kDa receptor for TNF, is much greater with membrane TNF than soluble TNF. However, if soluble TNF is produced as a tagged protein and crosslinked with an antibody against the tag, then it completely mimics the activities of membrane TNF [Schneider, 1998]. Finally, for CD40L, the stimulatory effects of a soluble form of this TNFSF protein are enhanced by crosslinking [Kehry, 1994] and yields an activity similar to membrane CD40L. For example, soluble CD40L-CD8 fusion protein requires crosslinking with a antibody to CD8 in order to drive resting B cells to proliferate to a degree similar to membrane-bound CD40L.). Even more strikingly, although membrane-bound CD40L expressed on baculovirus-transduced SF9 insect cells is a strong B cell stimulus, small vesicles (10-1,500 nm) prepared from the membranes of these cells are less stimulatory. However, ultracentrifugation of these vesicles creates aggregates which have the full activity of the original membrane CD40L protein. This indicates that B cells are more highly stimulated by a large surface of CD40L than they are by a smaller surface expressing this membrane ligand.

Taken together, the above reports suggest that, for some TNFSF/TNFRSF ligand/receptor pairs at least, it is essential to cluster receptors together for full signaling activity. By this interpretation, the efficacy of the membrane forms of FasL, TNF, and CD40L occurs because these ligands can move in the plane of the membrane toward the contact zone with a receptor-bearing responding cell, thereby clustering ligated receptors to form a receptor-dense region of the membrane. This interpretation is further supported by experiments where crosslinking of a soluble TNFSF protein effectively mimics the activity of the membrane form of the protein [Schneider, 1998].

In all of the above examples, no more than three amino acid chains have been caused to associate together. There is a need to produce multimeric protein molecules where more than three amino acid chains are caused to associate into a single soluble molecular complex. An important example comes from studies of CD40L (also called CD154 or TNFSF5), which is a member of the TNF family of molecules that are normally expressed as insoluble, cell membrane proteins. It has been shown that soluble homotrimers composed of the extracellular regions of CD40L, TNF, and FasL are not potently active on resting cells that bear receptors for these proteins. However, if these proteins are expressed with a tag on their ends (e.g., the FLAG peptide sequence) and then the trimers are extensively crosslinked using an antibody to FLAG, full activity appears (Schneider et al, *J. Exp. Med.* 187:1205, 1998). From this, it can be inferred that the soluble single-trimer forms of these molecules does not duplicate the multivalent interactions that normally occur when a receptor-bearing cell comes in contact with the membrane of a cell expressing numerous ligand trimers on its surface. This distinction may be due to a need for receptor clustering for full signaling (Bazzoni and Beutler, *N. Engl. J. Med.* 334:1717, 1996), which in turn is only possible with a multimeric ligand engaging many receptors at the same time in a localized region of the cell membrane.

SUMMARY OF THE INVENTION

The present invention contemplates a method of preparing soluble, multimeric mammalian proteins by culturing a host cell transformed or transfected with an expression vector encoding a fusion protein comprising the hub, body, and neck region of a collectin molecule and a heterologous mammalian protein.

In one embodiment, the heterologous mammalian protein comprises an extra cellular domain of a mammalian transmembrane protein; the resulting fusion protein forms a multimer.

In another embodiment, the heterologous mammalian protein comprises a soluble protein such as a cytokine; the resulting fusion protein forms a multimer.

In another embodiment, sites of proteolytic degradation are included or removed from the fusion protein; the resulting fusion protein forms a multimer from which are cleaved single units at a rate made variable by the nature of the proteolytic digestion sites either included or excluded.

In yet another embodiment, special attention is given to the immunogenicity of the fusion protein by altering the junction between the two naturally occurring proteins from which it is made; the resulting fusion protein may be less or more able to elicit an immune response against itself, which could lengthen its persistence or contribute to it immunological effectiveness.

A hybrid nucleotide sequence of no more than 1528 base pairs including a sequence defining a structural gene expressing a conjoined single strand of a multimeric TNFSF-SPD fusion protein, said structural gene having a nucleotide base sequence selected from members of the group consisting of SEQ ID NO 1, SEQ ID NO 3 and SEQ ID NO 5 is disclosed by this invention. In one embodiment, the DNA segment the structural gene has a sequence expressing a single hybrid amino acid chain of TNFSF-SPD, the segment having a first SPD nucleotide base sequence of SEQ ID NO 1, from base 32 to base 799, and a second sequence, expressing a portion of TNFSF stalk, selected from members of the group consisting of SEQ ID NO 1, from base 800 to base 1444, SEQ ID NO 3, from base 800 to base 1528, and SEQ ID NO 5, from base 800 to base 1441.

In another embodiment, a recombinant DNA molecule has vector operatively linked to an exogenous DNA segment defining a structural gene expressing a single amino acid chain of TNFSF-SPD. This structural gene has a nucleotide base sequence selected from members of the group consisting of SEQ ID NO 1, SEQ ID NO 3 and SEQ ID NO 5, any functional equivalents and modifications thereof. There is also attached an appropriate promoter for driving the expression of said structural gene in a compatible host organism. The organism can be *E. coli*, a yeast, a higher plant or animal.

Yet another embodiment contemplated by the invention is multimeric TNFSF-SPD fusion protein having a plurality of polypeptide trimers, a first trimer consisting of peptide strands of members of the TNF superfamily (TNFSF) of ligands, and a second trimer strand from a collectin molecule, each first trimer conjoined to a second polypeptide trimer strand from a collectin molecule, wherein said ligand strand is substituted for native carbohydrate recognition domains (CRD) of the collectin molecules. The conjoined collectin strands are covalently bound in parallel to each other, forming a multimeric fusion protein comprising a plurality of trimeric hybrid polypeptide strands radiating from a covalently bound center hub of the molecule. The free end of each trimeric radiating strand has a TNFSF moiety attached. The TNFSF moiety is one selected from the group consisting of ligands LTA, TNF, LTB, and TNFSF4 to TNFSF 18 as shown in Table II, and their functional equivalents, and modifications thereof.

The invention also contemplates a method for preparing a CD40-SPD multimeric fusion polypeptide, including the steps of initiating a culture, in a nutrient medium, of procaryotic or eucaryotic host cells transformed with a recombinant DNA molecule including an expression vector, appropriate for the cells, operatively linked to an exogenous DNA segment defining a structural gene for CD40-SPD ligand. The structural gene has a nucleotide base sequence of SEQ ID NO 1 from about base 32 to about base 1444. Thereafter, the culture is maintained for a time period sufficient for the cells to express the multimeric molecule.

Also contemplated is a method of producing a secreted, very large, biologically active, multimeric tumor necrosis factor superfamily ligand fusion protein chimera that is highly immunogenic and not readily diffusable. The steps for this method are as follows:

1. introducing into a host cell a first chimeric DNA construct including a transcriptional promoter operatively linked to a first secretory signal sequence, followed downstream by, and in proper reading frame with a first DNA sequence encoding a polypeptide chain of a first TNFSF ligand requiring multimerization for biological activity. This sequence is joined to a second DNA sequence encoding a collectin polypeptide at the site where the collectin's CRD was purposefully removed.

2. introducing into the host cell, a second DNA construct including a transcriptional promoter operably linked to a second secretory signal sequence followed downstream by, and in proper reading frame with, a third DNA sequence encoding a second polypeptide chain of a second TNFSF ligand joined to a fourth DNA sequence encoding a collectin polypeptide, wherein the collectin's CRD was purposefully removed, and then, 3. growing the host cell in an appropriate growth medium under physiological conditions to allow the secretion of a large multimerized polypeptide fusion protein, wherein the first polypeptide chain of a TNFSF-SPD protein is bound by parallel bonding of the respective collectin domain trimer to the second polypeptide chain of a different TNFSF-SPD polypeptide trimer, and wherein the multimerized polypeptide fusion protein exhibits biological activity characteristic of both membrane-attached TNFSFs, and 4. isolating the biologically active, multimerized TNFSF-SPD polypeptide fusion from said host cell. The chimeric reactant compounds are humanized to guard against destruction by a potential human recipient's immune system.

A final method of preparing a multimeric TNFSF-SPD ligand fusion protein contemplated requires a) preparing a first DNA segment coding for a strand of an exposed extracellular portion of TNFSF; b) preparing a second DNA segment coding for a collectin polypeptide strand, wherein the collectin's CRD domain of the strand has been removed; c) conjoining the first and second DNAs in proper reading frame, thereby creating a TNFSF-collectin DNA construct; d) inserting the construct into an expression vector system; e) introducing the vector system into an appropriate cell in culture under suitable conditions; f) harvesting and purifying spent medium from the culture; and finally g) assaying for presence of multimeric TNFSF-collectin fusion protein.

A method for stimulating the immune response in potentially immonocompetent cells using multimeric TNFSF fusion proteins by contacting the cells with the multimeric TNFSF fusion proteins, causing the cells to proliferate, is also contemplated. The cells used may be resting B cells. There is also a method for increasing antigenicity of cells by contacting the cells with the multimeric TNFSF fusion proteins. In this case, the cells may be tumor cells or HIV positive cells.

Other preferred embodiments contemplate the methods of preparation described above, wherein the host transformed is either a prokaryote, such as *E. coli*, a eukaryote, for example yeast, such as *S. cerevisiae*, or a higher plant, such as alfalfa or tobacco.

Still further embodiments and advantages of the invention will become apparent to those skilled in the art upon reading the entire disclosure contained herein.

DESCRIPTION OF THE PREFERRED EMBODIMENT

1. Definition of Terms

Figure 1:
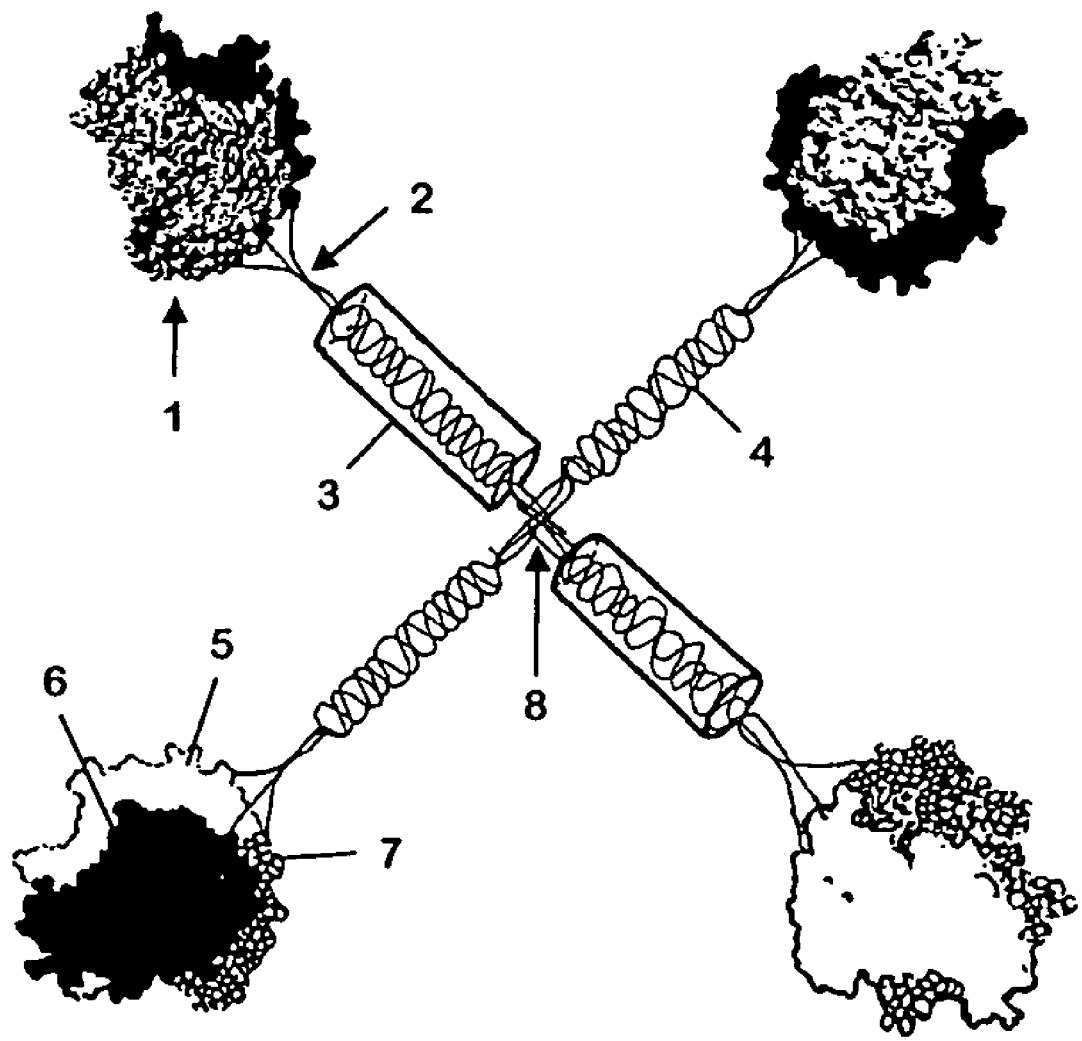
FIG. 1. Structure of the CD40L-SPD fusion protein. The extracellular portion of the CD40L homotrimer, including its membrane-proximal stalk, was fused to the body of SPD. The N-terminus of SPD contains two cysteines which link the homopolymer together by disulfide bonds forming a hub. The trimeric collagenous stalk extend from the hub as a cruciate structure and end in a spontaneously trimerizing neck region. The amino acid domains in a single chain of the CD40L-SPD are shown at the top. At the bottom is the tetrameric (four CD40L trimers) which is expected to form. In addition, the hub region of SPD can participate in stacking up to 8 or more cruciate forms into higher order aggregates.

Multimeric: As used herein the term multimeric refers to a multimer of a polypeptide that is itself a trimer (i.e., a plurality of trimers).

Functional Equivalent: Herein refers to a sequence of a peptide or polypeptide that has substantial structural similarity and functional similarity to another such sequence.

Modifications: Herein refers to point changes involving single amino acids, wherein the functionality is altered, without appreciably altering the primary sequence or primary structure of a peptide or polypeptide.

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| L | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagin |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues up to a total of about fifty residues in the polypeptide chain.

Base Pair (bp): A partnership of adenine (A) with thymine (T), or of cytosine (C) with guanine (G) in a double stranded DNA molecule.

Constitutive promoter: A promoter where the rate of RNA polymerase binding and initiation is approximately constant and relatively independent of external stimuli. Examples of constitutive promoters include the cauliflower mosaic virus 35S and 19S promoters described by Poszkowski et al., *EMBO J*, 3:2719 (1989) and Odell et al., *Nature*, 313:810 (1985).

DNA: Desoxyribonucleic acid.

Enzyme: A protein, polypeptide, peptide RNA molecule, or multimeric protein capable of accelerating or producing by catalytic action some change in a substrate for which it is often specific.

Expression vector: A DNA sequence that forms control elements that regulate expression of structural genes when operatively linked to those genes.

Expression: The combination of intracellular processes, including transcription and translation undergone by a structural gene to produce a polypeptide.

Insert: A DNA sequence foreign to the rDNA, consisting of a structural gene and optionally additional DNA sequences.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Operatively linked or inserted: A structural gene is covalently bonded in correct reading frame to another DNA (or RNA as appropriate) segment, such as to an expression vector so that the structural gene is under the control of the expression vector.

Polypeptide and peptide: A linear series of amino acid residues connected one to the other by peptide bonds between the alpha-amino and carboxy groups of adjacent residues.

Promoter: A recognition site on a DNA sequence or group of DNA sequences that provide an expression control element for a gene and to which RNA polymerase specifically binds and initiates RNA synthesis (transcription) of that gene.

Inducible promoter: A promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Spatially regulated promoter: A promoter where the rate of RNA polymerase binding and initiation is modulated in a specific structure of the organism such as the leaf, stem or root. Examples of spatially regulated promoters are given in Chua et al., Science, 244:174-181 (1989).

Spatiotemporally regulated promoter: A promoter where the rate of RNA polymerase binding and initiation is modulated in a specific structure of the organism at a specific time during development. A typical spatiotemporally regulated promoter is the EPSP synthase-35S promoter described by Chua et al., Science, 244:174-181 (1989).

Temporally regulated promoter: A promoter where the rate of RNA polymerase binding and initiation is modulated at a specific time during development. Examples of temporally regulated promoters are given in Chua et al., Science, 244:174-181 (1989).

Protein: A linear series of greater than about 50 amino acid residues connected one to the other as in a polypeptide.

Recombinant DNA molecule: A hybrid DNA sequence comprising at least two nucleotide sequences not normally found together in nature.

RNA: Ribonucleic acid.

Selective Genetic marker: A DNA sequence coding for a phenotypical trait by means of which transformed cells can be selected from untransformed cells.

Structural gene: A DNA sequence that is expressed as a polypeptide, i.e., an amino acid residue sequence.

Synthetic promoter: A promoter that was chemically synthesized rather than biologically derived. Usually synthetic promoters incorporate sequence changes that optimize the efficiency of RNA polymerase initiation.

2. Introduction

This invention discloses the production of TNFSF proteins as multimeric (i.e., many trimers) ligands fused onto a trimeric, branched protein backbone. Collectin molecules are ideal for this purpose because they are formed from many trimeric, collagenous arms linked to a central hub by disulfide bonds. Of the collecting, pulmonary surfactant protein D (SPD) was chosen initially because it is a homopolymer encoded by a single gene, unlike C1q and surfactant protein A, which are composed of two different protein subunits. In addition, recombinant SPD has been successfully expressed in vitro in reasonable yield [Crouch, 1994], and a peptide containing the "neck" region of SPD was shown to spontaneously trimerize in solution [Hoppe, 1994]. Consequently, extracellular domains of human and murine CD40L were substituted for the carbohydrate recognition domain of pulmonary surfactant D (SPD) to create a four-armed molecule (three peptide chains per arm) with CD40L at the end of each arm. This molecule is named CD40L-SPD. In addition, because SPD tends to stack into higher order aggregates with up to 8 molecules associated at the hub [Crouch], even greater degree of multimerization can occur [Lu, 1993]. CD40L-SPD therefore mimics the expression of CD40L by an activated T cell in that it presents a multivalent complex similar to membrane-bound CD40L. While remaining soluble, CD40L-SPD equals membrane CD40L in its range of activities.

3. Construction of expression plasmids for CD40L-SPD.

cDNAs of exposed human and murine CD40L, removed from cell membranes, were cloned by PCR by well-known methods. Murine surfactant protein D was cloned by hemi-nested PCR from murine lung mRNA (Clonetech). cDNA was prepared using Superscript II reverse transcriptase (Life Technologies, Gaithersburg, Md.) and random hexamers as primers. PCR primer sequences (SEQ ID NOS 7 through 15) were as follows (the underlined bases indicate restriction endonuclease sites for cloning into the vector):

mSPD5: 5'-CTGACATGCTGCCCTTTCTCTCCATGC-3' mSPD3ext: 5'-GGAGGCCAGCTGTCCTCCAGCCT-GTTTGC-3' rmSPD5: 5'-GGG G'CTAGCGAATTCCACCAGGAAGCAATCTGACATG CTGCCCTTT-CTCTCCATGC-3'

CD40L/SPD3: 5'-TCTATCTTGTCCAACCTTCTATG/GC-CATCAGGGAACAATGCAGCTTTC-3'

SPD/CD40L5: 5'-AAAGCTGCATTGTTCCCTGATGGC/CATAGAAGGTTGGACAAGATAGAAG-3'

CD40L3: 5'-GGGCTCGA GGTACCAGTTCTACATGCCTTGGAGTGTATAAT-3'

SPD/mCD40L5: 5'-GAAAGCTGCATTGTTCCCT-GATGGC/CATAGAAGATTGGATAAGGTCGAAG-3' mCD40L/SPD3: 5'-CTTCGACCTTATCCAATCTTC-TATG/GCCATCAGGGAACAATGCAGCTTTC-3' mCD40L3: 5'-GGGG GGTACCCTGCTGCAGCCTAGGACAGCGCAC-3'

Because the murine SPD sequence of the 5' untranslated region containing the ribosomal binding site was unknown when this work was started [Motwani, 1995], a primer (rmSPD5) was designed based on the available rat sequence [Shimizu, 1992] which extended the 5' end with rat sequence (shown in bold) along with an added Nhe I site (underlined).

4. Creation of the CD40L-SPD Fusions

To create the CD40L-SPD fusions, overlap PCR was used. Murine SPD was amplified by nested PCR using mSPD5 and mSPD3ext for the first round of 30 cycles. The product was diluted 1:1,000 and 1 μL was amplified for another 30 cycles using mSPD5 and CD40/SPD3, where the 3' half of CD40L/SPD3 is a reverse primer for SPD C-terminal to the neck region (deleting the CRD) and the 5' half of CD40L/SPD3 contains bases from the N-terminus of the extracellular portion of CD40L (immediately adjacent to the transmembrane region). Similarly, the CD40L plasmid was amplified with SPD/CD40L5 and CD40L3, which contains a Kpn I site (underlined). All of these PCRs were performed with Pfu cloned polymerase (Stratagene,) using hot start (Ampliwax, Perin-Elmer) and the thermocycling program: 94° C. for 2.5 min; then 30 cycles of 94° C. for 10 sec, 43° C. for 30 sec, and 75° C. for 7 min.

To form the chimeric construct, 1 µL of a 1:1,000 dilution of gel-purified products from the above reactions was combined and amplified with rmSPD5 and CD40L3. Because Pfu polymerase did not consistently yield the expected 1.62 kb overlap product, AccuTaq LA DNA polymerase (Sigma) was used for this PCR, using the thermocycling program: 94° C. for 2.5 min; then 30 cycles of 98° C. for 20 sec, 43° C. for 30, and 68° C. for 10 min. The resulting product was digested with Nhe I and Kpn I, gel-purified, and ligated into the Nhe I and Kpn I sites in the expression plasmid, pcDNA3.1(+) (Invitrogen, Carlsbad, Calif.). DH5 *E. coli* were transformed with the construct and plasmid DNA was purified either by double banding in ethidium bromide-CsCl gradients or by anion exchange resin (QIAgen). To form the T147N-CD40L-SPD construct, the same approach was used except that the CD40L coding region was taken from the expression plasmid for T147N-CD40L [Kombluth]. The amino acid sequence at the junction between SPD and CD40L is . . . KAALFPDG/HRRLDKIE . . . (SEQ ID NO:16), where the C-terminal portion begins the sequence for CD40L. To form mCD40L-SPD, a similar approach was taken except that primers SPD/mCD40L5, mCD40L/SPD3, and MCD40L3 were used for amplifications involving murine CD40L is . . . KAALFPDG/HRRLDKVE . . . (SEQ ID NO:17), where the C-terminal portion begins the sequence for murine CD40L. Both DNA strands of each construct were sequenced to confirm that the constructs were correct. In other experiments, an entirely humanized construct, consisting of human CD40L fused to human SPD, was constructed (data not shown).

5. Construction of Expression Plasmid for Murine RANKL/TRANCE (TNFSF 11).

Spleen cells from C3H/HeJ mice were stimulated with 5 µg/ml concanavalin A and 10 mg/ml IL-2 (Sigma) for 8 hours (31). mRNA was isolated using the Micro FastTrack kit (Invitrogen). cDNA was prepared using Superscript II reverse transcriptase (Life Technologies) and random hexamers as primers. PCR primers sequences (SEQ ID NOS 18 through 21) were as follows (where the underlined bases indicate restriction endonuclease sites for cloning into the vector):

5mRANKL-ext: 5'-CATGTTCCTGGCCCTCCTC-3'

3mRANKL-ext: 5'-GTACAGGCTCAAGAGAGAGGGC-3'

5mRANKL-int: 5'-ATACTCGAGCGCAGATGGATCCTAAC-3'

3mRANKL-int: 5'-GGGGTTTAGCGGCCGCTAATGTTCCACGAAATGAGTTC-3'

The extracellular portion of RANKL/TRANCE was cloned by nested PCR. In the first round of PCR, 5mRANKL-ext and 3MRANKL-ext were used with Pfu cloned polymerase (Stragene) using the thermocycling program: 94° C. for 2.5 min; then 30 cycles of 94° C. for 10 sec, 50° C. for 30 sec, and 75° C. for 2 min. The product was diluted 1:1,000 and 1 µL was amplified for another 30 cycles using 5mRANKL-int and 3mRANK-int, which contain an Xho I site and a Not I site respectively. The resulting product was digested with Xho I, blunt-ended with T4 DNA polymerase, then digested with Not I and gel-purified. The CD40L-SPD expression plasmid described above was digested with Msc I an Not I and gel purified. Then the RANKL/TRANCE sequence was ligated into this vector in frame with the SPD coding sequence. The amino acid sequence at the junction between SPD and RANKL/TRANCE is . . . KAALFPDG/RAQMDPNR . . . (SEQ ID NO:22), where the N-terminal portion is from SPD and the C-terminal portion is the extracellular sequence of RANKL/TRANCE. Both DNA strands of each construct were sequenced to confirm that the constructs were correct.

6. Stable Transfection of DHFR-Deficient CHO Cells and Amplification.

DG44 (a line of CHO-$K^1$ cells deficient in dihydrofolate reductase (DHFR)) (32) and pCH1P (a plasmid containing the hamster DHFR minigene) (33) were gifts from Dr. Lawrence Chasin, Columbia University, New York, N.Y. DG44 cells were cultured in α-MEM consisting of ribo- and deoxynucleoside-free α-MEM (BioWhittaker, Walkersville, Md.) supplemented with 200 µM L-glutamine, 10% fetal bovine serum (FBS) and 10 µg/ml each of adenosine, deoxyadenosine, and thymidine (Sigma). All cell cultures described were negative in a mycoplasma rRNA assay (Gen-Probe, San Diego). DG44 cells in six-well plates were transfected by the method of Okayama and Chen ((34) with 10 µg of expression plasmid and 0.05 µg of pCH1P (200:1 ratio). After two days, the transfected DG44 were trypsinized and transferred to 100 mm plates. At this point, the media was switched to α⁻-MEM which differs from α-MEM in that dialyzed FBS (HyClone Systems, Logan, Utah) was used and no nucleoside supplements were added. Only cells containing the DHFR minigene were able to grow in α⁻-MEM, and colonies were selected after 10 days, cloned using cloning rings, and transferred to 12.5 $cm^2$ flasks. Clones were selected for expansion using an ELISA to screen for the production of either murine or human CD40L (see below). Using the method described by Kingston et al. (35), escalating doses of methotrexate were used to amplify the transfected genes over a period of 6-14 months until the cells grew well in 80 µM methotrexate. Each expressing clone was re-cloned once or twice more in order to select the highest expressing cells.

7. Preparation of Human and Murine CD40L-SPD in Serum-Free Media.

Selected clones were adapted for growth in nucleoside-free UltraCHO media (BioWhittaker) supplemented with 50-100 µg/mL ascorbic acid and 50 µM methotrexate (Sigma). The non-adherent population was further adapted for suspension growth in roller bottles. In some experiments, the cells were adapted from α⁻-MEM to CHO-S-SFM II media (Life Technologies) supplemented with ascorbic acid and 50 µg/mL L-proline.

8. ELISA Assay for Human and Murine CD40L-SPD

To assay for correctly folded CD40L, wells of a MaxiSorb 96-well plate (Nunc) were coated overnight at 4° C. with 50 µL of carbonate-bicarbonate, pH 9.40 buffer containing 0.5 µg/mL 24-31 anti-human CD40L MAb (Ancell) or MRI anti-murine MAb (Bioexpress, Lebanon, N.H.). Wells were blocked with 3% bovine serum albumin (BSA) in PBS. 100 µL samples were added to the wells either neat or diluted in a dilution buffer consisting of 1% BSA, 0.9% NaCl, 50 mM Tris pH 7.40, and 0.1% peroxide-free Tween 20 (Sigma). After shaking for 2 h at 600 RPM, a plate washer was used to wash the plate four times with 0.9% NaCl, 50 mM Tris pH 7.40, and 0.1% peroxide-free Tween 20. Then, 100 µL of diluent buffer containing 1 µg/mL biotinylated 24-31 anti-human CD40L Mab (Ancell) or MR1 anti-murine CD40L Mab (Pharmingen, San Diego, Calif.) was added to each well and again shaken for 2 h. Following another four washer, 100 µL of diluent buffer containing 1 µg/mL of streptavidin-alkaline phosphatase (Jackson) was added to each well and the plate was shaken for 1 hour. Lastly, after another four washes, color was developed for 10-20 min using 100 µL/well of BluePhos (Kierkegaard & Perry), stop solution was added, and the wells were read at 650 µm in a plate reader.

9. Purification of Human and Murine CD40L-SPD.

Conditioned UltraCHO media was filtered using a 0.2 µl PES filter unit (Nalgene) and stored at 4° C. for up to 3 months. A preliminary size fractionation was performed by ultrafiltration through a 100 kDa-cutoff 76 mm membrane (YM-100, Millipore) in a 400 mL stirred cell at 10 lbs/sq. inch pressure of argon. Media was concentrated to about 10 mL, diluted to 100 mL with buffer, and again concentrated to 10 mL for a total of 3 cycles of ultrafiltration and buffer exchange. Buffer was 50 mM Bicine (Calbiochem), adjusted to pH 9.0 with NaOH (about 32 mM Na), and 1 mM EDTA to prevent the activity of any metalloproteinase. Using FPLC equipment (Amersham-Pharmacia), the concentrate was filtered through a 0.45 µl filter, placed into a 10 mL superloop, applied to a 10×30 mm column (HR10/30, Amersham-Pharmacia) packed with Fractogel $SO_3^-$650M (EM Biosciences), and eluted at 0.5 mL/min at 4° C. with a linear gradient of 0-500 mM NaCl in buffer. As described by the manufacturer, the resolution of proteins on Fractogel $SO_3^-$ is enhanced by using a long, thin column geometry. Fractions were collected and screened for human or murine CD40L by ELISA. Positive fractions were pooled, concentrated by ultrafiltration (CentriPrep-30, Millipore), filtered through a 0.45µ filter, and applied to a Superose 6 column (Amersham-Pharmacia) in phosphate-buffered saline.

10. Murine B Cell Cultures.

C3H/HeJ mice were euthanized by $CO_2$ inhalation under a protocol approved by the Animal Subjects Committee of the San Diego VA Healthcare System. Splenocytes were isolated by centrifugation over Lympholyte-M (Accurate Chemical & Scientific Corp. Westbury, N.Y.) and B cells were isolated by negative selection using anti-CD43 immunomagnetic beads (Miltenyi Biotec Inc. Auburn. CA). The resting B cells were suspended in Dulbecco's MEM with 10% FBS at a concentration of $1\times10^6$/mL, and 100 µL was added to the wells of 96-well flat-bottomed plates. 100 µL of dilutions of murine CD40L-SPD in media or media alone were added to the wells, which were incubated in 8.5% $CO_2$ at 37° C. for 48 hours. Then, 0.5 µCi/well of $^3$H-thymidine was added to each well, and the cells were collected 4 h later onto glass fiber filters using an automated cell harvester. A scintillation counter was used to determine the incorporated radioactivity.

11. Human B cell cultures.

Venous blood from consenting subjects was used as a source of human B cells under a protocol approved by the UCSD Institutional Review Board. Blood was collected into syringes containing 5 U/mL heparin and peripheral blood mononuclear cells (PBMC) were isolated by centrifugation over Ficoll-hypaque. The cells were suspended at $2\times10^5$/mL in RPMI 1640 containing 200 µM L-glutamine, 10% FBS, 0.832 µM cyclosporin A (Sigma), and 25 ng/mL human IL-4 (R & D Systems) and incubated in 5% $CO_2$ at 37° C. as described by Schultze et al. (36). At intervals, the cells were stained with CyChrome-conjugated anti-CD19 and PE-conjugated anti-CD80 (B7-1) monoclonal antibodies (Pharmingen) and analyzed by flow cytometry.

12. Human Monocyte-Derived Macrophage and Dendritic Cell Cultures.

As previously described [Kombluth], monocytes were isolated from PBMC by adherence to fibronectin-mated plates, plated into 48-well plates, and then cultured in RPMI1640 containing 200 µM L-glutamine and 10% autologous serum for 7-10 days. Monolayers of the matured cells (about $2\times10^5$/well), termed monocyte-derived macrophages or MDM, were then washed in media and cultured in 1 mLIwell RPMI1640 containing 200 µM L-glutamine and 10% heat-inactivated FBS. Alternatively, dendritic cells (DC) were formed from monocytes by adding GM-CSF and IL-4 to the culture media, and the resulting DC were used 6 days later. Preparations of CD40L-SPD were added to the wells as indicated. As a positive control, 100 ng/mL bacterial lipopolysaccharide (LPS) from *E. coli* 0111:B4 (Calbiochem) was added. Supernatants were collected 24 h later and analyzed for cytokine content using ELISA (R & D Systems).

EXAMPLE 1

Design Principles in Constructing Collectin-TNFSF Member Fusion Proteins.

To express CD40L and other TNFSF members as stable, multimeric proteins, the coding region of the extracellular, C-terminal portion of CD40L was joined in-frame to the collectin, surfactant protein D(SPD). The N-terminus of SPD contains two cysteines which form the disulfide bonds necessary for the 4-armed cruciate structure of the overall molecule [Brown-Augsburger, 1996]. C-terminal to these cysteines in SPD is a long triple-helical collagenous "stalk" which ends in the "neck" region that promotes the trimerization of each arm of the structure. Immediately after this neck region, the coding sequence for the extracellular portion of CD40L was added, in place of the carbohydrate recognition domain (CRD) of SPD. The collectins were chosen as the framework for the multimeric construct because of their multi-subunit structure and the trimeric nature of their stalk regions. Appropriateness of replacing the CRD of a collectin with the extracellular region of a TNFSF member is further supported by structural studies of the two protein families. An analysis of the CRD crystal structure of another collectin, ACRP30, indicated that it was structurally superimposable upon the crystal structures of the extracellular regions of CD40L, TNF, and Fas [Shapiro, 1998]. The successful expression of the collectin-TNFSF fusion protein, CD40L-SPD, indicates that other TNFSF members (Table I) could be conjoined to SPD in a similar manner and that other collectins besides SPD (Table II) could be used as a protein framework instead of SPD. Because these molecules are formed entirely from naturally occurring proteins, the production of an immune response (e.g., antibodies) to these fusion proteins is minimized. By deleting portions of the stalk region of the TNFSF proteins, additional constructs can be made which may be even less immunogenic.

EXAMPLE 2

Expression of Human and Murine CD40L-SPD in CHO Cells.

The coding regions for the extracellular portion of human CD40L, human T147N-CD40L, an inactive mutant of CD40L, or murine CD40L were joined to the neck region of murine SPD, replacing the SPD CRD (FIG. 1). A CMV-driven expression plasmid for the construct was co-transfected with a DHFR minigene into DNFR-deficient CHO cells. Following selection in nucleoside-free media, expressing CHO clones were amplified by culture in ascending doses of methotrexate. The resulting clones produced about 1-10 µg/mL of the fusion protein over a 3 day period in media containing FBS.

Clones were adapted for growth as suspension cells in two types of serum-free media. Murine CHO-SPD produced in UltraCHO (BioWhittaker) was largely retained (about 60% as determined by ELISA) by a 1,000 kDa cutoff ultrafiltration membrane (Pall Corp., Port Washington, N.Y.), consistent with a large multimeric complex formed by the stacking of the SPD portion of the molecule. However, in CHO-S-SFM II (Life Technologies), nearly all ELISA-detectable murine CHO-SPD passed through a 100 kDa cutoff ultrafiltration membrane (Millipore), suggesting that the protein was either folding incorrectly in this media or was being degraded by proteolysis. Consequently, the purification method was optimized for the spent UltraCHO media.

EXAMPLE 3

Purification of human and murine CD40L-SPD.

Figure 2:
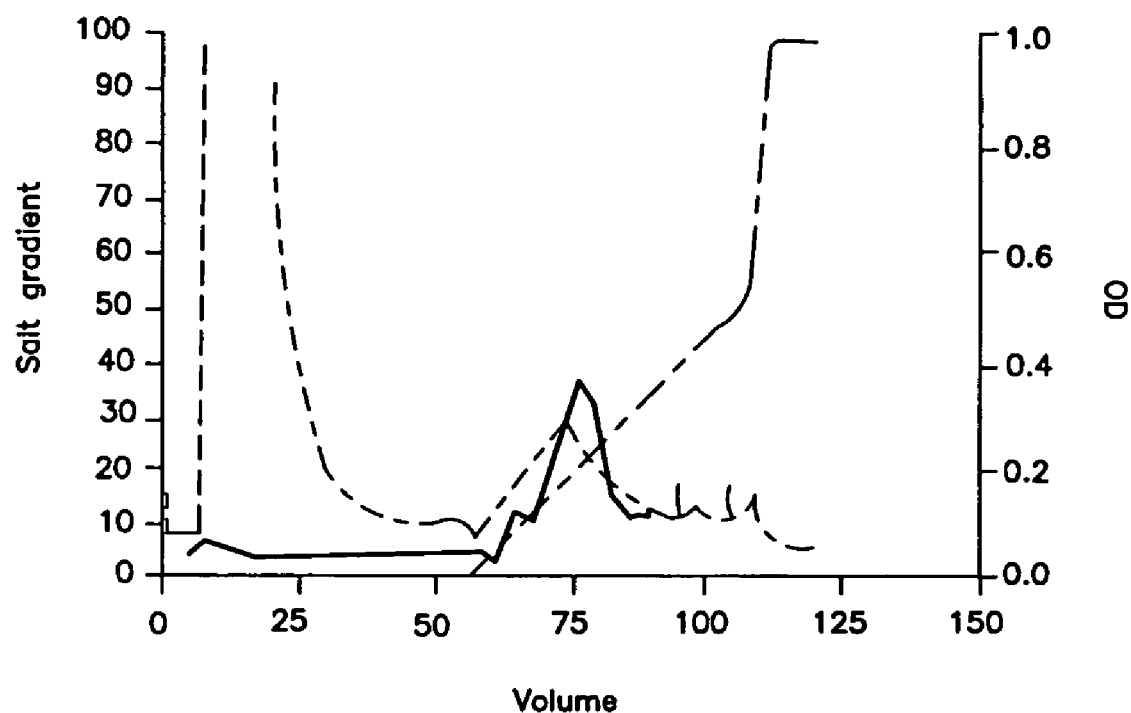
FIG. 2. Ion-exchange chromatography of murine CD40L-SPD. CHO cells expressing murine CD40L-SPD were grown in serum-free media, concentrated using a 100 kDa cutoff ultrafiltration membrane, and diafiltered into 50 mM bicine, pH 9.0, 1 mM EDTA. Using an FPLC system, the protein from 400 mL of media was applied to a Fractogel $SO_3^-$650M column and eluted with a linear salt gradient. 3 mL samples were collected. Shown are curves for protein concentration ($OD_{280}$), conductivity as % 1 M NaCl in the buffer, and ELISA-detectable CD40L-SPD assayed at 1:100 dilution.
Figure 3:
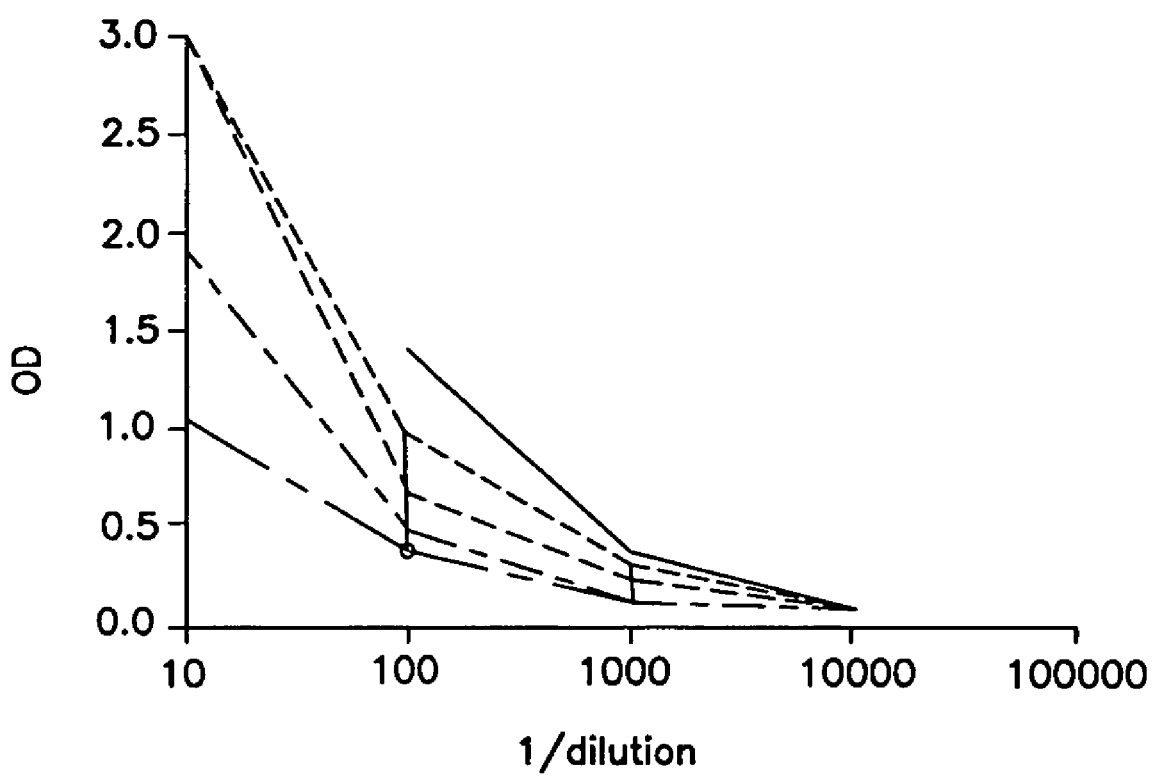
FIG. 3. Size fractionation of murine CD40L-SPD by ultrafiltration. CD40L-SPD is a 471 amino acid protein with a predicted molecular weight of 49,012 for each of the twelve component chains in the dodecamer (composed of four trimeric subunits). This does not include added carbohydrates. Therefore, the full dodecamer will have a molecular weight in excess of 600,000. However, from the literature on recombinant surfactant protein D made in CHO cells, it appears that some of the product will be in the form of trimers that are not part of a cruciate-formed dodecamer. To determine what percentage of CD40L-SPD was produced in a multimeric form, supernatant from the transfected CHO cells were passed through filters of different porosities (rated for their ability to retard globular proteins). An ELISA was used to detect the amount of CD40L-SPD (measured at multiple dilutions) that passed through the filter. As shown, about 90% of the protein is retained by a 300,000 kDa cut-off filter. This indicates that most of the protein is in the dodecameric form. In addition, the cruciate dodecamers of surfactant protein D can also stack on top of each other into even higher molecular weight forms. This is the likely explanation for the small fraction of CD40L-SPD that is retained by the 1,000 kDa cut-off filter.

Purification procedures were developed for murine CD40L-SPD, but the same methods could be applied to human CD40L-SPD with minor modifications. Murine CD40L-SPD has a predicted m.w. of 49 kDa per chain, or about 600 kDa per 12-chain, cruciate molecule, the amino acid sequence predicts a pI of 9.10. Accordingly, conditioned media was concentrated by ultrafiltration through a 100 kDa cutoff filter, which also fractionates the sample on a size basis. After diafiltration into 50 mM bicine, pH 9.00 (also containing 1 mM EDTA added to inhibit metalloproteinases), the sample was applied to a variety of cationic exchange resins. Using Source 30S (Amersham-Pharmacia), most of the ELISA-detectable protein did not bind and was recovered in the flow-through. However, as reported by Morris et al. {Morris}, Fractogel $SO_3$ 650M retained the protein. The retention by this tentacular resin and not by Source 30S suggests binding to positively charged residues that are not on the protein surface. Using a linear NaCl gradient, ELISA-detectable protein elutes at between 0.15-0.30 M NaCl under these conditions (FIG. 2). In selected experiments, the protein was further purified using a Superose 6 sizing column. Most of the ELISA-detectable protein eluted in the excluded volume, indicating an apparent m.w. of greater than 1,000 kDa (FIG. 3).

EXAMPLE 4

Activity of CD40L-SPD on Human B Cells.

Figure 4:
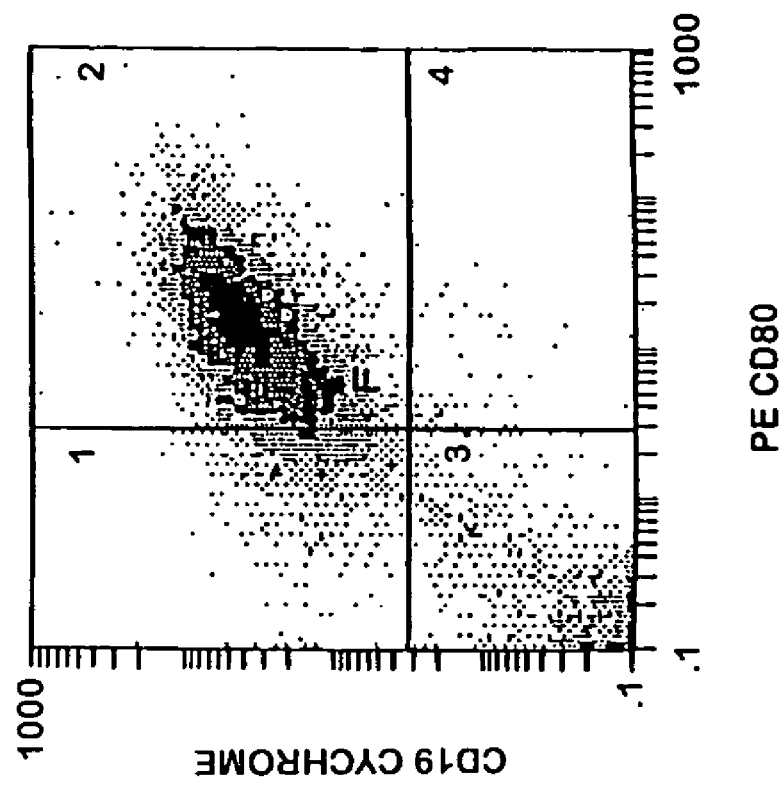
FIG. 4. Activation of human B cells by human CD40L-SPD. Conditioned media from CHO cells expressing human CD40L-SPD was added to human B cells along with IL-4. In the left panel, the cells were stained with CyChrome-labeled anti-CD 19 to identify B cells and PE-labeled anti-CD3 to identify T cells. As shown, most of the cells proliferating in the culture were CD19+CD3−B cells. In the right panel, the cells were stained with CyChrome-labeled anti-CD19 to identify B cells and PE-labeled anti-CD80 (B7-1) to identify this co-stimulatory molecule. As shown, almost all of the B cells were induced by CD40L-SPD to express CD80.
Figure 4:
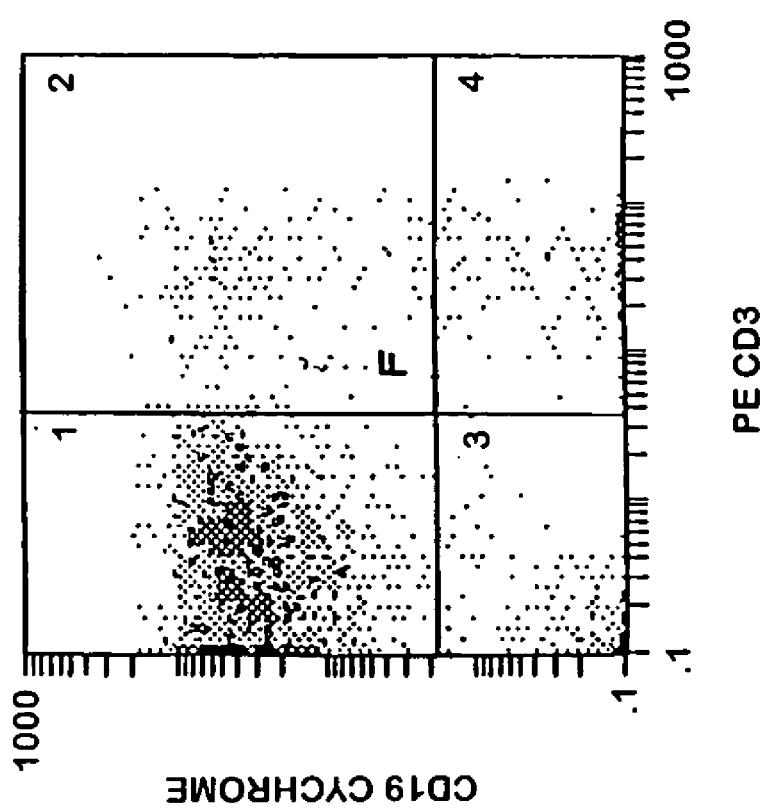

Schultze et al. described a system using CD40L-expressing cells plus IL-4 and cyclosporin A (to inhibit T cell growth) as a means to grow very large numbers of B cells from a small sample of blood. Because CD40L activates these B cells to express high levels of B7 molecules (CD80 and CD86), the proliferating B cells were effective in presenting peptide antigens and rival non-dividing dendritic cells as antigen-presenting cells (APCs) (36). To determine if the CD40L-SPD fusion protein could replace CD40L-expressing cells in this system, PBMC were cultured with CD40L-SPD in addition to IL-4 and cyclosporin A. Under these conditions the cells grew to saturation density every three days. After three weeks, the cultures were almost entirely CD 19+B cells which express high levels of CD80 (FIG. 4). This indicates that CD40L-SPD can be used in ex vivo systems where a soluble yet effective form of CD40L is needed to stimulate cells for immunotherapeutic applications.

EXAMPLE 5

Activity of CD40L-SPD on murine B cells.

Figure 5:
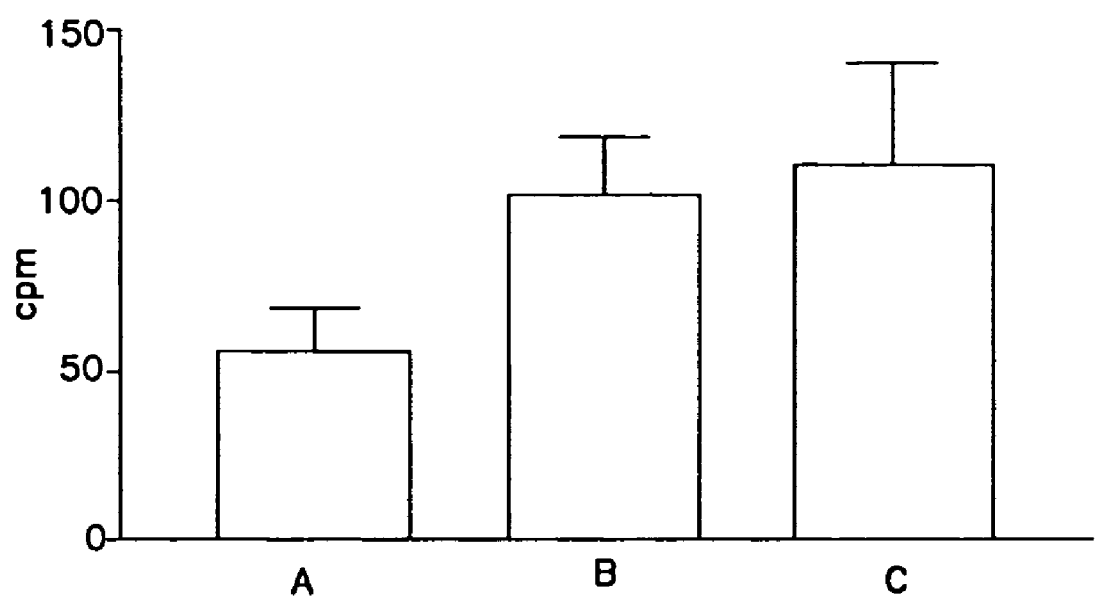
FIG. 5. Activation of murine B cells by murine CD40L-SPD. Murine CD40L-SPD was added to resting murine splenic B cells for a two day culture period. For the final 4 hours, the cultures were pulsed with ³H-thymidine, following which the cells were harvested and DNA synthesis was measured by scintillation counting. As shown, CD40L-SPD is nearly as effective as anti-IgM in promoting the proliferation of resting B cells.

Resting murine B cells are particularly difficult to stimulate with most soluble forms of CD40L. Even with murine CD40L-CD8 fusion proteins, it is necessary to crosslink the protein with antibodies against CD8 in order to achieve maximal proliferation in culture [Klauss, 1999]. Accordingly, resting murine B cells were negatively selected with immunomagnetic beads. As shown in FIG. 5, murine CD40L-SPD was as effective as anti-IgM antibody in driving B cells to proliferate. This indicates that CD40L-SPD can mimic the multivalent interactions that occur when a responding cell comes in contact with CD40L-bearing activating cells.

EXAMPLE 6

Activity of CD40L-SPD on human macrophages and dendritic cells.

Figure 6:
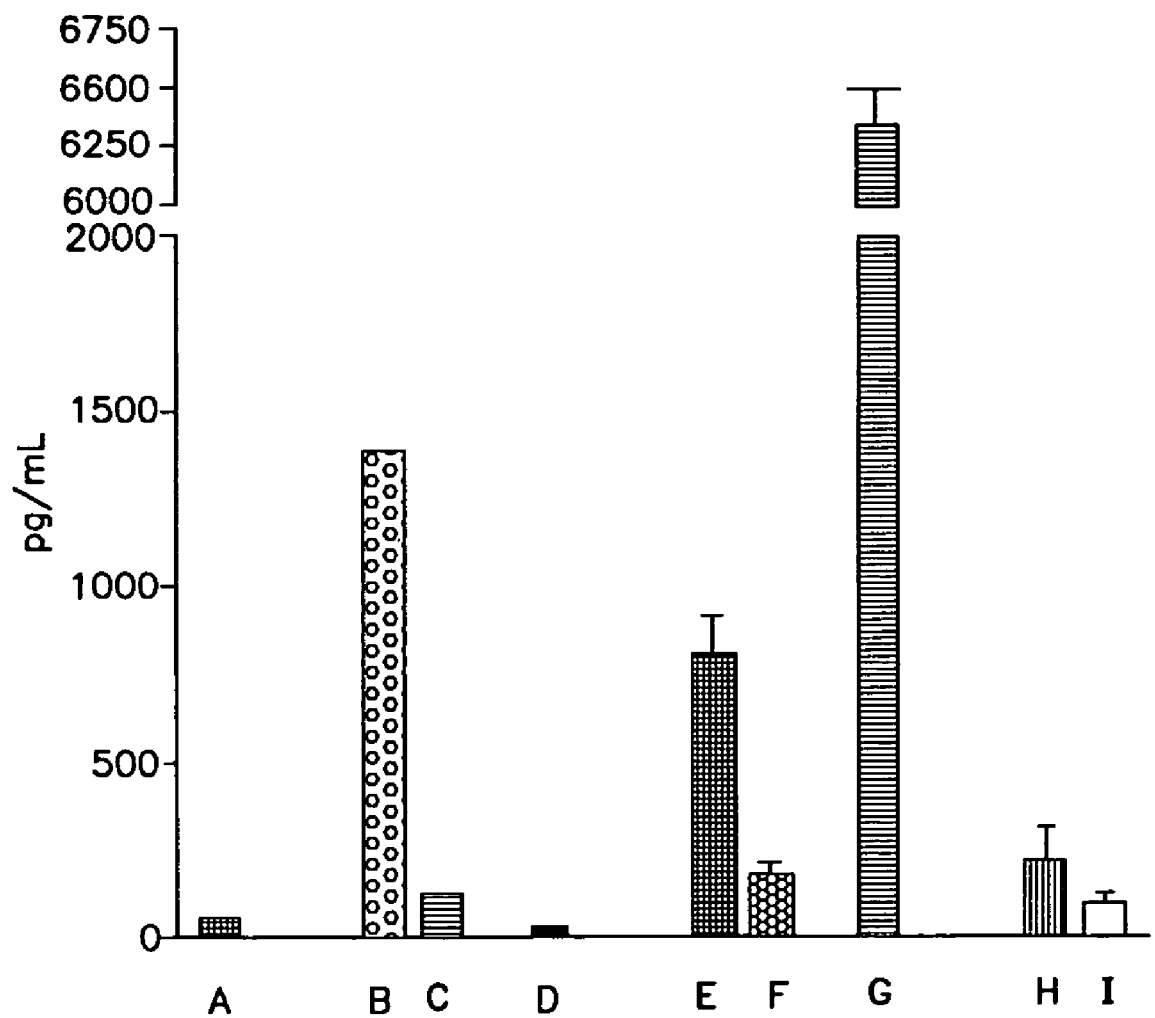
FIG. 6. CD40L-SPD stimulation of macrophage chemokine production. Conditioned media from CHO cells expressing human CD40L-SPD, an inactive mutant of human CD40L-SPD (T147N-CD40L-SPD), or murine CD40L-SPD (mCD40L-SPD) were added to cultures of human monocyte-derived macrophages. As a negative control, this media was heat-inactivated at 60° C. for 30 minutes. Also shown is a form of soluble CD40L (sCD40L) consisting of 149 amino acids from the extracellular domain of human CD40L (Peprotech) added at 1 ?g/mL. 24 hours later, supernatants were collected and assay for MIP-1? by ELISA (R & D Systems). The weak activity of soluble single-trimer CD40L (sCD40L) is apparent. In contrast, native human and murine CD40L-SPD strongly activated the macrophages to produce MIP-1?. In contrast, heat-inactivated CD40L-SPD was inactive. As expected, the inactive mutant, T147N-CD40L-SPD, also failed to stimulate macrophages, demonstrating that the CD40L portion and not the SPD portion of the protein was responsible for stimulating the macrophages.
Figure 7:
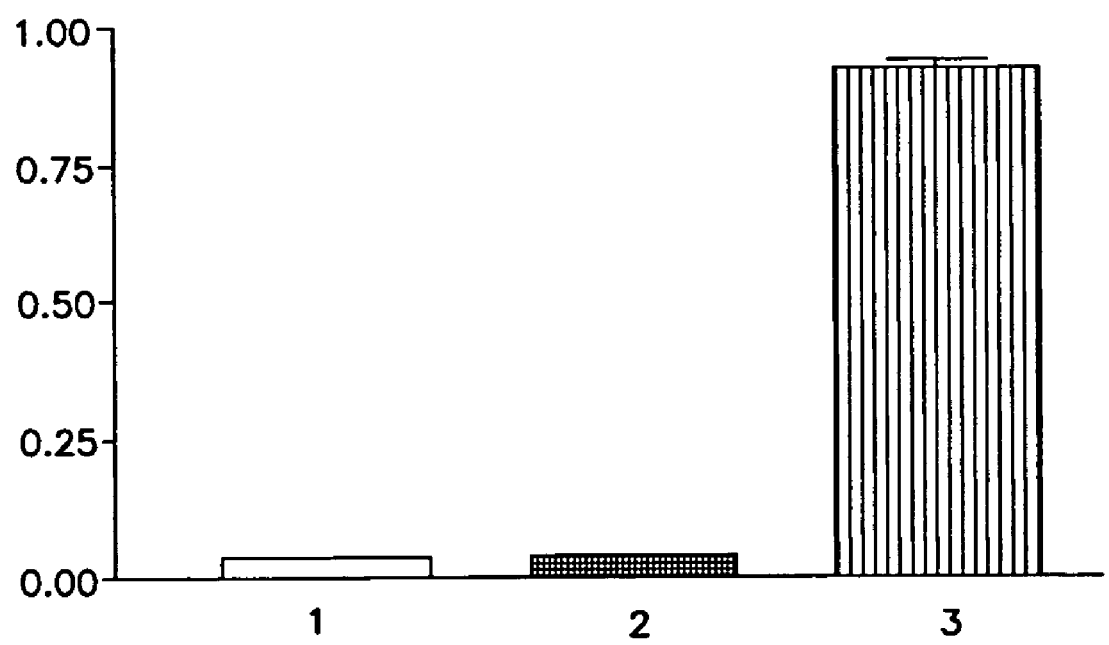
FIG. 7. Expression of RANKL/TRANCE-SPD production from CHO cells detected by ELISA. Antibodies against RANKL/TRANCE were used to construct an ELISA capable of detecting the RANKL/TRANCE protein. As shown, there was no background with the media control. Using a fusion protein between CD70 (CD27L or TNFSF7) and SPD, there was also no signal, indicating the specificity of the ELISA. However, using CHO cells transfected with an expression plasmid for CD70-SPD, immunoreactive secreted protein was clearly detectable. This demonstrates the generalizability of the method for expressing TNFSF members as fusion proteins with collectins such as SPD.

CD40L is a powerful stimulant for macrophages (reviewed in (28)) and dendritic cells (40). Accordingly, preparations of CD40L-SPD were added to monocyte-derived macrophages and the production of MIP-1β was used as a measure of stimulation. As shown in FIG. 6, both human and murine CD40L-SPD were able to stimulate macrophages, whereas the T147N-CD40L-SPD mutant was inactive as expected.

DISCUSSION

These examples define a new method of producing multimeric (i.e., many trimers) of CD40L as a fusion protein with SPD. Also prepared and expressed were similar fusion proteins between murine RANKL/TRANCE (TNFSF11) or murine CD27L/CD70 (TNFSF7) joined to murine SPD (data not shown). This suggests that virtually all TNFSF members could be successfully produced as fusion proteins with SPD. Furthermore, it is also likely that other collectins besides SPD could be used in these fusions, given the strong structural homologies between the CRDs of the collectins and the extracellular domains of TNFSF members [Shapiro] which can be substituted for these CRDs. Given the 17 known TNFSF members and 9 known collecting, at least 153 fusion protein combinations are possible.

SPD was selected for initially because it is a soluble homopolymer. Other collectins, such as surfactant protein A, have strong binding affinities to lipids and specific cell receptors. Although removal of the CRD abrogates much of this binding, it may be partially mediated by the neck region sequence, which the fusion proteins retain. Accordingly, it would be expected that collectins other than SPD might confer different cell-binding and pharmacokinetic behaviors upon a fusion protein. For example, macrophages are known to take up and degrade whole SPD [Dong, 1998]. If a fusion protein other than SPD were used, the disposition of the fusion protein in vivo might be altered. Additionally, metalloproteinases are known to degrade the collectin, C1q, so that a fusion with C1q may alter the degradation of the fusion protein. For example, because CD40L activates macrophages and other cells to produce metalloproteinases, which could potentially degrade the collagenous portion of SPD and other collecting. Cleavage of the collagenous stalk would then be expected to release single-trimers of CD40L, which could diffuse away from the original parent molecule, much like a slow-release formulation of a drug. Also, the membrane-proximal portion of CD40L has been retained in CD40L-SPD. This sequence also contains protease-susceptible amino acid sequences, which can be eliminated by mutagenesis to retard the cleavage of CD40L from the fusion protein. Mutations in such proteinase cleavage site(s) would delay such cleavage and favor the local persistence of the CD40L stimulus.

CD40L-SPD is a large macromolecule (>1,000 kDa), and the other TNFSF-collectin fusion proteins would be expected to be similarly large. For native SPD, the aggregates that spontaneously form measure 100 nm in diameter. When injected into tissue, this large a complex would be expected to remain at the injection site for a prolonged period. Localization of the TNFSF-containing protein would also be expected to reduce any systemic toxicity caused by the release of free single-trimers into the circulation. For example, soluble CD40L in blood has been linked to disease activity in lupus, and this smaller molecule may even cross the glomerulus to cause damage to renal tubules [Kato and Kipps, J. Clin. Invest. November 1999]. On the other hand, because CD40L induces the production of chemokines which attract immune cells [Kombluth], T cells, monocytes, and dendritic cells would be expected migrate to the site where CD40L-SPD was injected. This might be advantageous if CD40L-SPD were used as a vaccine adjuvant. In mice, soluble CD40L (sCD40LT) stimulates IgG1 production but not cytotoxic T lymphocytes (CTLs) [Wong, 1999]. Interestingly, the same protein that is expressed from an injected plasmid stimulates both a strong antibody and CTL response [Gurunathan, 1998]. In the latter case, the plasmid would be expected to deliver a localized supply of CD40L, whereas the sCD40LT protein is free to diffuse away. Support for the localized use of CD40L in an adjuvant formulation is provided by a study using a plasmid expressing full-length membrane CD40L, which was very effective in stimulating both humoral and CTL immune responses [Mendoza, 1997]. Similarly, injection of adenovirus expressing membrane CD40L has potent antitumor activity in mice [Kikuchi, 1999]. Similar considerations would likely apply to other fusion proteins between the TNFSF and collecting.

Finally, for immunostimulatory proteins, it is particularly important that the protein not be antigenic if repeated injections are needed. For example, vaccination with TNF-μ modified by the addition of short peptide sequences was able to induce the production of disease-modifying anti-TNF-μ autoantibodies [Dalum, 1999]. Because CD40L-SPD and other TNFSF-collectin fusion proteins are formed from endogenous protein sequences (with the possible exception of the peptide sequence at the junction), the production of antibodies might not limit the effectiveness of repeated injections.

In conclusion, fusions between TNFSF members and collectins offer a novel means of generating large protein complexes which can provide localized stimulation at an injection site. Because of the multimeric nature of the collectin backbone, such fusion proteins may mimic the multivalent ligand surface presented by the membrane forms of TNFSF members to TNFRSF-bearing responding cells. Moreover, by limiting systemic toxicity while maintaining localized efficacy, such fusion proteins may have a role as vaccine adjuvants against infectious agents and tumors.

TABLE I

Ligands of the TNF Superfamily*

| New Ligand Symbol | Other Names | Genbank ID |
|---|---|---|
| LTA | Lymphotoxin-, TNF-a, TNFSF1 | X01393 |
| TNF | TNF-a, TNFSF2 | X02910 |
| LTB | Lymphotoxin-, TNFSF3 | L11016 |
| TNFSF4 | OX-40L | D90224 |
| TNFSF5 | CD40L, CD154. Gp39, T-BAM | X67878 |
| TNFSF6 | FasL | U11821 |
| TNFSF7 | CD27L, CD70 | L08096 |
| TNFSF8 | CD30L | L09753 |
| TNFSF9 | 4-1BBL | U03398 |
| TNFSF10 | TRAIL, Apo-2L | U37518 |
| TNFSF11 | RANKL, TRANCE, OPGL, ODF | AF013171 |
| TNFSF12 | TWEAK, Apo-3L | AF030099 |
| TNFSF13 | APRIL | NM_003808 |
| TNFSF13B | BAFF, THANK, BLYS | AF136293 |
| TNFSF14 | LIGHT, HVEM-L | AF036581 |
| TNFSF15 | VEGI | AF039390 |
| TNFSF16 | unidentified | |
| TNFSF17 | unidentified | |
| TNFSF18 | AITRL, GITRL | AF125303 |

*(as of Nov. 1, 1999) Known members of ligands in the TNF superfamily, taken from the Human Gene Nomenclature Committee

TABLE II

The Collectin Superfamily

| | |
|---|---|
| C1q | Pulmonary surfactant protein D |
| Mannose-binding protein, MBL1 | conglutinin |
| Mannose-binding protein, MBL2 | collectin-43 |
| | CL-L1 |
| Pulmonary surfactant protein A | ACRP30 |
| | Hib27 |

All collectins are formed as multimers of trimeric subunits, each containing a collagenous domain. The C-terminus of each collectin contains a CRD which binds carbohydrates and other ligands. Because of the tight similarities between the known CRD structures and the extracellular domains of TNFSF members, it is likely that the CRD of any collectin could be replaced with the extracellular domain of any TNFSF member in a structurally compatible manner.

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

REFERENCES

Banchereau, J., and R. M. Steinman. 1998. Dendritic cells and the control of immunity. *Nature* 392:245-252.

Bazzoni, F., and B. Beutler. 1996. The tumor necrosis factor ligand and receptor families. *New England Journal of Medicine* 334:1717-1725.

Brown-Augsburger, P., K. Hartshorn, D. Chang, K. Rust, C. Fliszar, H. G. Welgus, and E. C. Crouch. 1996. Site-directed mutagenesis of Cys-15 and Cys-20 of pulmonary surfactant protein D. Expression of a trimeric protein with altered anti-viral properties. *Journal of Biological Chemistry* 271:13724-13730.

Chen, C. A., and H. Okayama. 1988. Calcium phosphate-mediated gene transfer: a highly efficient transfection system for stably transforming cells with plasmid DNA. *Biotechniques* 6:632-638.

Crouch, E., A. Persson, D. Chang, and J. Heuser. 1994. Molecular structure of pulmonary surfactant protein D (SP-D). *Journal of Biological Chemistry* 269:17311-17319.

Crouch, E., D. Chang, K. Rust, A. Persson, and J. Heuser. 1994. Recombinant pulmonary surfactant protein D. Post-translational modification and molecular assembly. *Journal of Biological Chemistry* 269:15808-15813.

Crouch, E. C. 1998. Structure, biologic properties, and expression of surfactant protein D (SP-D). *Biockimica et Biophysica Acta* 1408:278-289.

Dalum, I, D. M. Butler, M. R. Jensen, P. Hindersson, L. Steinaa, A. M. Waterston, S. N. Grell, M. Feldmann, H. I. Eisner, and S. Mouritsen. 1999. Therapeutic antibodies elicited by immunization against TNF-alpha. *Nature Biotechnology* 17:666-669.

Dhodapkar, M. V., R. M. Steinman, M. Sapp, H. Desai, C. Fossella, J. Krasovsky, S. M. Donahoe, P. R. Dunbar, V. Cerundolo, D. F. Nixon, and N. Bhardwaj. 1999. Rapid generation of broad T-cell immunity in humans after a single injection of mature dendritic cells. *Journal of Clinical Investigation* 104:173-180.

Dong, Q., and J. R. Wright. 1998. Degradation of surfactant protein D by alveolar macrophages. *American Journal of Physiology* 274:L97-105.

Fanslow, W. C., S. Srinivasan, R. Paxton, M. G. Gibson, M. K. Spriggs, and R. J. Armitage. 1994. Structural characteristics of CD40 ligand that determine biological function. *Seminars in Immunology* 6:267-278.

Grell, M., E. Douni, H. Wajant, M. Lohden, M. Clauss, B. Maxeiner, S. Georgopoulos, W. Lesslauer, G. Kollias, K. Pfizenmaier, and et al. 1995. The transmembrane form of tumor necrosis factor is the prime activating ligand of the 80 kDa tumor necrosis factor receptor. *Cell* 83:793-802.

Gruss, H. J., and S. K. Dower. 1995. Tumor necrosis factor ligand superfamily: involvement in the pathology of malignant lymphomas. *Blood* 85:3378-3404.

Gurunathan, S., K. R. Irvine, C. Y. Wu, J. I. Cohen, E. Thomas, C. Prussin, N. P. Restifo, and R. A. Seder. 1998. CD40 ligand/trimer DNA enhances both humoral and cellular immune responses and induces protective immunity to infectious and tumor challenge. *Journal of Immunology* 161:4563-4571.

Higgins, L. M., S. A. McDonald, N. Whittle, N. Crockett, J. G. Shields, and T. T. MacDonald. 1999. Regulation of T cell activation in vitro and in vivo by targeting the OX40-OX40 ligand interaction: amelioration of ongoing inflammatory bowel disease with an OX40-IgG fusion protein, but not with an OX40 Hgand-IgG fusion protein. *Journal of Immunology* 162:486-493.

Hollenbaugh, D., N. J. Chalupny, and A. Aruffo. 1992. Recombinant globulins: novel research tools and possible pharmaceuticals. *Current Opinion in Immunology* 4:216-219.

Hoppe, H. J., and K. B. Reid. 1994. Collectins-soluble proteins containing collagenous regions and lectin domains—and their roles in innate immunity. *Protein Science* 3:1143-1158.

Hoppe, H. J., P. N. Barlow, and K. B. Reid. 1994. A parallel three stranded alpha-helical bundle at the nucleation site of collagen triple-helix formation. *Febs Letters* 344:191-195.

Kato, K., E. Santana-Sahagun, L. Rassenti, M. Weisman, N. Tamura, S. Kobayashi, H. Hashimoto, and T. Kipps. 1999. The soluble CD40 ligand sCD154 in systemic lupus erythematosus. *J. Clin. Invest.* 104:947-955.

Kehry, M., B. Castle, and P. Hodgkin. 1992. B-cell activation mediated by interactions with membranes from helper T cells. In Mechanisms of Lymphocyte Activation and Immune Regulation IV: Cellular Communications, vol. 323. S. Gupta and T. Waldmann, editors. Plenum Press, New York. 139.

Kehry, M. R., and B. E. Castle. 1994. Regulation of CD40 ligand expression and use of recombinant CD40 ligand for studying B cell growth and differentiation. *Seminars in Immunology* 6:287-294.

Kikuchi, T., and R. G. Crystal. 1999. Anti-tumor immunity induced by in vivo adenovirus vector-mediated expression of CD40 ligand in tumor cells. *Human Gene Therapy* 10:1375-1387.

Kingston, R., R. Kaufman, C. Bebbington, and M. Rolfe. 1999. Amplification using CHO expression vectors. In Current Protocols in Molecular Biology, vol. 3. F. Ausubel, R. Brent, R. Kingston, D. Moore, J. Seidman, J. Smithe and K. Struhl, editors. 4 vols. John Wiley & Sons, Inc., New York. 16.14.11-16.14.13.

Klaus, G. G., M. Holman, C. Johnson-Leger, J. R. Christenson, and M. R. Kehry. 1999. Interaction of B cells with activated T cells reduces the threshold for CD40-mediated B cell activation. *International Immunology* 11:71-79.

Kombluth, R. S., K. Kee, and D. D. Richman. 1998. CD40 ligand (CD154) stimulation of macrophages to produce HIV-1-suppressive beta-chemokines. *Proceedings of the National Academy of Sciences of the United States of America* 95:5205-5210.

Kuroki, Y., and D. R. Voelker. 1994. Pulmonary surfactant proteins. *Journal of Biological Chemistry* 269:25943-25946.

Kwon, B., B. S. Youn, and B. S. Kwon. 1999. Functions of newly identified members of the tumor necrosis factor receptor/ligand superfamilies in lymphocytes. *Current Opinion in Immunology* 11.340-345.

Lane, P., T. Brocker, S. Hubele, E. Padovan, A. Lanzavecchia, and F. McConnell. 1993. Soluble CD40 ligand can replace the normal T cell-derived CD40 ligand signal to B cells in T cell-dependent activation. *Journal of Experimental Medicine* 177:1209-1213.

Lu, J., H. Wiedemann, U. Holmskov, S. Thiel, R. Timpl, and K. B. Reid. 1993. Structural similarity between lung surfactant protein D and conglutinin. Two distinct, C-type lectins containing collagen-like sequences. *European Journal of Biochemistry* 215:793-799.

Mach, F., U. Schonbeck, J. Y. Bonnefoy, J. S. Pober, and P. Libby. 1997. Activation of monocyte/macrophage functions related to acute atheroma complication by ligation of CD40: induction of collagenase, stromelysin, and tissue factor. *Circulation* 96:396-399.

Malik, N., B. W. Greenfield, A. F. Wahl, and P. A. Kiener. 1996. Activation of human monocytes through CD40 induces matrix metalloproteinases. *Journal of Immunology* 156:3952-3960.

Mariani, S. M., B. Matiba, T. Spama, and P. H. Krammer. 1996. Expression of biologically active mouse and human CD95/APO-1/Fas ligand in the baculovirus system. *Journal of Immunological Methods* 193:63-70.

Mendoza, R. B., M. J. Cantwell, and T. J. Kipps. 1997. Immunostimulatory effects of a plasmid expressing CD40 ligand (CD 154) on gene immunization. *Journal of Immunology* 159:5777-5781.

Morris, A. E., R. L. Remmele, Jr., R. Klinke, B. M. Macduff, W. C. Fanslow, and R. J. Armitage. 1999. Incorporation of an isoleucine zipper motif enhances the biological activity of soluble CD40L (CD154). *Journal of Biological Chemistry* 274:418-423.

Motwani, M., R. A. White, N. Guo, L. L. Dowler, A. I. Tauber, and K. N. Sastry. 1995. Mouse surfactant protein-D. cDNA cloning, characterization, and gene localization to chromosome 14. *Journal of Immunology* 155:5671-5677.

Oyaizu, N., N. Kayagaki, H. Yagita, S. Pahwa, and Y. Dcawa. 1997. Requirement of cell-cell contact in the induction of Jurkat T cell apoptosis: the membrane-anchored but not soluble form of FasL can trigger anti-CD3-induced apoptosis in Jurkat T cells. *Biochemical and Biophysical Research Communications* 238:670-675.

Pietravalle, F., S. Lecoanet-Henchoz, J. P. Aubry, G. Elson, J. Y. Bonnefoy, and J. F. Gauchat. 1996. Cleavage of membrane-bound CD40 ligand is not required for inducing B cell proliferation and differentiation. *European Journal of Immunology* 26:725-728.

Pullen, S. S., M. E. Labadia, R. H. Ingraham, S. M. McWhirter, D. S. Everdeen, T. Alber, J. J. Crute, and M. R. Kehry. 1999. High-affinity interactions of tumor necrosis factor receptor-associated factors (TRAFs) and CD40 require TRAF trimerization and CD40 multimerization. *Biochemistry* 38:10168-10177.

Ruiz, S., A. H. Henschen-Edman, H. Nagase, and A. J. Tenner. 1999. Digestion of C1q collagen-like domain with MMPs-1,-2,-3, and -9 further defines the sequence involved in the stimulation of neutrophil superoxide production. *Journal of Leukocyte Biology* 66:416-422.

Schneider, P., N. Holler, J. L. Bodmer, M. Hahne, K. Frei, A. Fontana, and J. Tschopp. 1998. Conversion of membrane-bound Fas(CD95) ligand to its soluble form is associated with downregulation of its proapoptotic activity and loss of liver toxicity. *Journal of Experimental Medicine* 187: 1205-1213.

Schuchmann, M., S. Hess, P. Bufler, C. Brakebusch, D. Wallach, A. Porter, G. Riethmuller, and H. Engelmann. 1995. Functional discrepancies between tumor necrosis factor and lymphotoxin alpha explained by trimer stability and distinct receptor interactions. *European Journal of Immunology* 25:2183-2189.

Schultze, J. L., S. Michalak, M. J. Seamon, G. Dranoff, K. Jung, J. Daley, J. C. Delgado, J. G. Gribben, and L. M. Nadler. 1997. CD40-activated human B cells: an alternative source of highly efficient antigen presenting cells to generate autologous antigen-specific T cells for adoptive immunotherapy. *Journal of Clinical Investigation* 100: 2757-2765.

Seyama, K., S. Nonoyama, I. Gangsaas, D. Hollenbaugh, H. F. Pabst, A. Aruffo, and H. D. Ochs. 1998. Mutations of the CD40 ligand gene and its effect on CD40 ligand expression in patients with X-linked hyper IgM syndrome. *Blood* 92:2421-2434.

Shapiro, L., and P. E. Scherer. 1998. The crystal structure of a complement-Iq family protein suggests an evolutionary link to tumor necrosis factor. *Current Biology* 8:335-338.

Shimizu, H., J. H. Fisher, P. Papst, B. Benson, K. Lau, R. J. Mason, and D. R. Voelker. 1992. Primary structure of rat pulmonary surfactant protein D. cDNA and deduced amino acid sequence. *Journal of Biological Chemistry* 267:1853-1857.

Smith, C. A., T. Farrah, and R. G. Goodwin. 1994. The TNF receptor superfamily of cellular and viral proteins: activation, costimulation, and death. *Cell* 76:959-962.

Suda, T., H. Hashimoto, M. Tanaka, T. Ochi, and S, Nagata. 1997. Membrane Fas ligand kills human peripheral blood T lymphocytes, and soluble Fas ligand blocks the killing. *Journal of Experimental Medicine* 186:2045-2050.

Tesselaar, K., L. A. Gravestein, G. M. van Schijndel, J. Borst, and R. A. van Lier. 1997. Characterization of murine CD70, the ligand of the TNF receptor family member CD27. *Journal of Immunology* 159:4959-4965.

Urlaub, G., E. Kas, A. M. Carothers, and L. A. Chasin. 1983. Deletion of the diploid dihydrofolate reductase locus from cultured mammalian cells. *Cell* 33:405-412.

Venolia, L., G. Urlaub, and L. A. Chasin. 1987. Polyadenylation of Chinese hamster dihydrofolate reductase genomic genes and minigenes after gene transfer. *Somatic Cell and Molecular Genetics* 13:491-504.

Wong, B. R., R. Josien, S. Y. Lee, B. Sauter, H. L. Li, R. M. Steinman, and Y. Choi. 1997. TRANCE (tumor necrosis factor [TNF]-related activation-induced cytokine), a new TNF family member predominantly expressed in T cells, is a dendritic cell-specific survival factor. *Journal of Experimental Medicine* 186:2075-2080.

Wong, C. P., C. Y. Okada, and R. Levy. 1999. TCR vaccines against T cell lymphoma: QS-21 and IL-12 adjuvants induce a protective CD8+ T cell response. *Journal of Immunology* 162:2251-2258.

Zipp, F., R. Martin, R. Lichtenfels, W. Roth, J. Dichgans, P. H. Krammer, and M. Weller. 1997. Human autoreactive and foreign antigen-specific T cells resist apoptosis induced by soluble recombinant CD95 ligand. *Journal of Immunology* 159:2108-2115.

What is claimed is:

1. A soluble multimeric polypeptide of at least two trimer units, wherein each trimer unit comprises a fusion protein trimer strand consisting of:

a first polypeptide comprising the first about 100 to 250 N-terminus residues of a collectin family scaffold protein, wherein the first polypeptide comprises a hub and a body region of the collectin family scaffold protein; and a second polypeptide comprising the last about 100 to 250 C-terminus residues of a tumor necrosis factor superfamily (TNFSF) ligand, wherein the second polypeptide comprises an extracellular domain (ECD) of the TNFSF ligand, wherein the carboxy-terminal residue of the first polypeptide is operably linked to the amino-terminal residue of the second polypeptide via:

i) deletion of a carbohydrate recognition domain (CRD) of the collectin family scaffold protein and ii) replacement of the CDR with the ECD of the TNFSF ligand, whereby a single trimer strand spontaneously trimerizes with two additional trimer strands to form a trimer unit and the trimer unit binds at the hub to form the multimeric polypeptide.

2. The multimeric polypeptide of claim 1, wherein the TNFSF ligand is selected from lymphotoxin-A (LTA), lymphotoxin-B (LTB), tumor necrosis factor (TNF), or any of TNFSF4-15 and TNFSF18.

3. The multimeric polypeptide of claim 1, wherein the collectin family scaffold protein is selected from complement factor 1(C1q), mannose binding protein, mannose-binding lectin type 1(MBL1), mannose-binding lectin type 2 (MBL2), pulmonary surfactant protein A (SPA), pulmonary surfactant protein D (SPD), conglutinin, collectin 43, C-type lectin L1(CL-L1), adipocyte complement related protein of 30 kDa (ACRP30), or hibernation specific protein 27 (Hib27).

4. The multimeric polypeptide of claim 1, wherein the trimer unit comprises homomeric trimer strands.

5. The multimeric polypeptide of claim 1, wherein the trimer unit comprises heteromeric trimer strands.

6. The multimeric polypeptide of claim 1, wherein the collectin family scaffold protein is surfactant protein D.

7. The multimeric polypeptide of claim 1, wherein the TNFSF ligand is CD40L.

8. The multimeric polypeptide of claim 1, wherein the trimer strand is SPD-CD40L.

9. The multimeric polypeptide of claim 1, wherein the TNFSF ligand is receptor activator of NF-kappaB ligand (RANKL).

10. The multimeric polypeptide of claim 1, wherein the trimer strand is SPD-RANKL.

11. The multimeric polypeptide of claim 1, wherein the TNFSF ligand is CD27L/CD70.

12. The multimeric polypeptide of claim 1, wherein the trimer strand is SPD-CD27L/CD70.

13. The multimeric polypeptide of claim 1, wherein amino acid residues comprising the trimerized strands which are susceptible to proteolytic degradation are removed from the multimeric polypeptide.

14. The multimeric polypeptide of claim 1, wherein the multimer is a dimer of trimer units.

* * * * *

SEQUENCE LISTING

```
<160> NUMBER OF SEQ ID NOS: 22

<210> SEQ ID NO 1
<211> LENGTH: 1552
<212> TYPE: DNA
<213> ORGANISM: Artificial Sequence
<220> FEATURE:
```

```
<223> OTHER INFORMATION: Murine surfactant protein D (without the CRD)
      fused to the extracellular portion of human CD40L
<220> FEATURE:
<221> NAME/KEY: 5'UTR
<222> LOCATION: (7)..(31)
<220> FEATURE:
<221> NAME/KEY: CDS
<222> LOCATION: (32)..(1444)
<220> FEATURE:
<221> NAME/KEY: sig_peptide
<222> LOCATION: (32)..(88)
<223> OTHER INFORMATION: Signal peptide from murine surfactant protein D
<220> FEATURE:
<221> NAME/KEY: misc_feature
<222> LOCATION: (88)..(799)
<223> OTHER INFORMATION: Mature murine surfactant protein D including
      hub region, collagenous portion, and neck, but excluding
      carbohydrate recognition domain (CRD)
<220> FEATURE:
<221> NAME/KEY: misc_feature
<222> LOCATION: (801)..(1546)
<223> OTHER INFORMATION: Human CD40 ligand extracellular region,
      including stalk.
<300> PUBLICATION INFORMATION:
<301> AUTHORS: Motwani M
<302> TITLE: Mouse surfactant protein-D. cDNA cloning,
      characterization, and gene localization to chromosome 14.
<303> JOURNAL: J. Immunol.
<304> VOLUME: 155
<305> ISSUE: 12
<306> PAGES: 5671 TO 5677
<307> DATE: 1995
<313> RELEVANT RESIDUES: (32)..(802)
<300> PUBLICATION INFORMATION:
<301> AUTHORS: Spriggs MK
<302> TITLE: Recombinant human CD40 ligand stimulates B cell
      proliferation and immunoglobulin E secretion
<303> JOURNAL: Journal of Experimental Medicine
<304> VOLUME: 176
<305> ISSUE: 6
<306> PAGES: 1543-1550
<307> DATE: 1992
<313> RELEVANT RESIDUES: (803)..(1552)

<400> SEQUENCE: 1
gctagcgaat tccaccagga agcaatctga c atg ctg ccc ttt ctc tcc atg        52
                                   Met Leu Pro Phe Leu Ser Met
                                    1               5 ctt gtc ttg ctt gta cag ccc ctg gga aat ctg gga gca gaa atg aag     100
Leu Val Leu Leu Val Gln Pro Leu Gly Asn Leu Gly Ala Glu Met Lys
        10                  15                  20 agc ctc tcg cag aga tca gta ccc aac acc tgc acc cta gtc atg tgt     148
Ser Leu Ser Gln Arg Ser Val Pro Asn Thr Cys Thr Leu Val Met Cys
 25                  30                  35 agc cca aca gag aat ggc ctg cct ggt cgt gat gga cgg gat ggg aga     196
Ser Pro Thr Glu Asn Gly Leu Pro Gly Arg Asp Gly Arg Asp Gly Arg
 40                  45                  50                  55 gaa ggt cca cgg ggt gag aag ggt gat cca ggt ttg cca gga cct atg     244
Glu Gly Pro Arg Gly Glu Lys Gly Asp Pro Gly Leu Pro Gly Pro Met
                 60                  65                  70 ggg ctc tca ggg ttg cag ggc cct aca ggt cca gtt gga ccc aaa gga     292
Gly Leu Ser Gly Leu Gln Gly Pro Thr Gly Pro Val Gly Pro Lys Gly
         75                  80                  85 gag aat ggc tct gct ggc gaa cct gga cca aag gga gaa cgt gga cta     340
Glu Asn Gly Ser Ala Gly Glu Pro Gly Pro Lys Gly Glu Arg Gly Leu
     90                  95                 100 agt gga cct cca gga ctt cca ggt att cct ggt cca gct ggg aaa gaa     388
Ser Gly Pro Pro Gly Leu Pro Gly Ile Pro Gly Pro Ala Gly Lys Glu
105                 110                 115 ggt ccc tct ggg aag cag ggg aac ata gga cct caa ggc aaa cca ggt     436
```

```
Gly Pro Ser Gly Lys Gln Gly Asn Ile Gly Pro Gln Gly Lys Pro Gly
120             125                 130                 135 cct aaa gga gag gct ggg ccc aaa gga gaa gta ggt gct cct ggc atg      484
Pro Lys Gly Glu Ala Gly Pro Lys Gly Glu Val Gly Ala Pro Gly Met
                140                 145                 150 caa gga tct aca ggg gca aaa ggc tcc aca ggc ccc aag gga gaa aga      532
Gln Gly Ser Thr Gly Ala Lys Gly Ser Thr Gly Pro Lys Gly Glu Arg
            155                 160                 165 ggt gcc cct ggt gtg caa gga gcc cca ggg aat gct gga gca gca gga      580
Gly Ala Pro Gly Val Gln Gly Ala Pro Gly Asn Ala Gly Ala Ala Gly
        170                 175                 180 cct gcc gga cct gcc ggt cca cag gga gct cca ggt tcc agg ggg ccc      628
Pro Ala Gly Pro Ala Gly Pro Gln Gly Ala Pro Gly Ser Arg Gly Pro
    185                 190                 195 cca gga ctc aag ggg gac aga ggt gtt cct gga gac aga gga atc aaa      676
Pro Gly Leu Lys Gly Asp Arg Gly Val Pro Gly Asp Arg Gly Ile Lys
200                 205                 210                 215 ggt gaa agc ggg ctt cca gac agt gct gct ctg agg cag cag atg gag      724
Gly Glu Ser Gly Leu Pro Asp Ser Ala Ala Leu Arg Gln Gln Met Glu
                220                 225                 230 gcc tta aaa gga aaa cta cag cgt cta gag gtt gcc ttc tcc cac tat      772
Ala Leu Lys Gly Lys Leu Gln Arg Leu Glu Val Ala Phe Ser His Tyr
            235                 240                 245 cag aaa gct gca ttg ttc cct gat ggc cat aga agg ttg gac aag ata      820
Gln Lys Ala Ala Leu Phe Pro Asp Gly His Arg Arg Leu Asp Lys Ile
        250                 255                 260 gaa gat gaa agg aat ctt cat gaa gat ttt gta ttc atg aaa acg ata      868
Glu Asp Glu Arg Asn Leu His Glu Asp Phe Val Phe Met Lys Thr Ile
    265                 270                 275 cag aga tgc aac aca gga gaa aga tcc tta tcc tta ctg aac tgt gag      916
Gln Arg Cys Asn Thr Gly Glu Arg Ser Leu Ser Leu Leu Asn Cys Glu
280                 285                 290                 295 gag att aaa agc cag ttt gaa ggc ttt gtg aag gat ata atg tta aac      964
Glu Ile Lys Ser Gln Phe Glu Gly Phe Val Lys Asp Ile Met Leu Asn
                300                 305                 310 aaa gag gag acg aag aaa gaa aac agc ttt gaa atg caa aaa ggt gat     1012
Lys Glu Glu Thr Lys Lys Glu Asn Ser Phe Glu Met Gln Lys Gly Asp
            315                 320                 325 cag aat cct caa att gcg gca cat gtc ata agt gag gcc agc agt aaa     1060
Gln Asn Pro Gln Ile Ala Ala His Val Ile Ser Glu Ala Ser Ser Lys
        330                 335                 340 aca aca tct gtg tta cag tgg gct gaa aaa gga tac tac acc atg agc     1108
Thr Thr Ser Val Leu Gln Trp Ala Glu Lys Gly Tyr Tyr Thr Met Ser
    345                 350                 355 aac aac ttg gta acc ctg gaa aat ggg aaa cag ctg acc gtt aaa aga     1156
Asn Asn Leu Val Thr Leu Glu Asn Gly Lys Gln Leu Thr Val Lys Arg
360                 365                 370                 375 caa gga ctc tat tat atc tat gcc caa gtc acc ttc tgt tcc aat cgg     1204
Gln Gly Leu Tyr Tyr Ile Tyr Ala Gln Val Thr Phe Cys Ser Asn Arg
                380                 385                 390 gaa gct tcg agt caa gct cca ttt ata gcc agc ctc tgc cta aag tcc     1252
Glu Ala Ser Ser Gln Ala Pro Phe Ile Ala Ser Leu Cys Leu Lys Ser
            395                 400                 405 ccc ggt aga ttc gag aga atc tta ctc aga gct gca aat acc cac agt     1300
Pro Gly Arg Phe Glu Arg Ile Leu Leu Arg Ala Ala Asn Thr His Ser
        410                 415                 420 tcc gcc aaa cct tgc ggg caa caa tcc att cac ttg gga gga gta ttt     1348
Ser Ala Lys Pro Cys Gly Gln Gln Ser Ile His Leu Gly Gly Val Phe
    425                 430                 435
```

-continued

```
gaa ttg caa cca ggt gct tcg gtg ttt gtc aat gtg act gat cca agc     1396
Glu Leu Gln Pro Gly Ala Ser Val Phe Val Asn Val Thr Asp Pro Ser
440                 445                 450                 455 caa gtg agc cat ggc act ggc ttc acg tcc ttt ggc tta ctc aaa ctc     1444
Gln Val Ser His Gly Thr Gly Phe Thr Ser Phe Gly Leu Leu Lys Leu
            460                 465                 470 tgaacagtgt caccttgcag gctgtggtgg agctgacgct gggagtcttc ataatacagc   1504
acaggcttaa gcccaattat acactccaag gcatgtagaa ctggtacc                1552
```

<210> SEQ ID NO 2
<211> LENGTH: 471
<212> TYPE: PRT
<213> ORGANISM: Artificial Sequence
<220> FEATURE:
<223> OTHER INFORMATION: Synthetic Construct

<400> SEQUENCE: 2

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
            35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
                100                 105                 110

Pro Gly Pro Ala Gly Lys Glu Gly Pro Ser Gly Lys Gln Gly Asn Ile
            115                 120                 125

Gly Pro Gln Gly Lys Pro Gly Pro Lys Gly Glu Ala Gly Pro Lys Gly
    130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
    195                 200                 205

Pro Gly Asp Arg Gly Ile Lys Gly Glu Ser Gly Leu Pro Asp Ser Ala
210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Ile Glu Asp Glu Arg Asn Leu His Glu Asp
            260                 265                 270

Phe Val Phe Met Lys Thr Ile Gln Arg Cys Asn Thr Gly Glu Arg Ser
    275                 280                 285

Leu Ser Leu Leu Asn Cys Glu Glu Ile Lys Ser Gln Phe Glu Gly Phe
    290                 295                 300
```

```
                             -continued
Val Lys Asp Ile Met Leu Asn Lys Glu Glu Thr Lys Lys Glu Asn Ser
305                 310                 315                 320

Phe Glu Met Gln Lys Gly Asp Gln Asn Pro Gln Ile Ala Ala His Val
                325                 330                 335

Ile Ser Glu Ala Ser Ser Lys Thr Thr Ser Val Leu Gln Trp Ala Glu
                340                 345                 350

Lys Gly Tyr Tyr Thr Met Ser Asn Asn Leu Val Thr Leu Glu Asn Gly
            355                 360                 365

Lys Gln Leu Thr Val Lys Arg Gln Gly Leu Tyr Tyr Ile Tyr Ala Gln
        370                 375                 380

Val Thr Phe Cys Ser Asn Arg Glu Ala Ser Ser Gln Ala Pro Phe Ile
385                 390                 395                 400

Ala Ser Leu Cys Leu Lys Ser Pro Gly Arg Phe Glu Arg Ile Leu Leu
                405                 410                 415

Arg Ala Ala Asn Thr His Ser Ser Ala Lys Pro Cys Gly Gln Gln Ser
                420                 425                 430

Ile His Leu Gly Gly Val Phe Glu Leu Gln Pro Gly Ala Ser Val Phe
            435                 440                 445

Val Asn Val Thr Asp Pro Ser Gln Val Ser His Gly Thr Gly Phe Thr
        450                 455                 460

Ser Phe Gly Leu Leu Lys Leu
465                 470

<210> SEQ ID NO 3
<211> LENGTH: 1574
<212> TYPE: DNA
<213> ORGANISM: Artificial Sequence
<220> FEATURE:
<223> OTHER INFORMATION: Murine surfactant protein D (except CRD) fused
      to the extracellular domain of murine RANKL/TRANCE
<220> FEATURE:
<221> NAME/KEY: 5'UTR
<222> LOCATION: (7)..(31)
<220> FEATURE:
<221> NAME/KEY: misc_feature
<222> LOCATION: (32)..(799)
<223> OTHER INFORMATION: Murine surfactant protein D including hub
      region, collagenous portion, and neck, but excluding carbohydrate
      recognition domain (CRD)
<220> FEATURE:
<221> NAME/KEY: CDS
<222> LOCATION: (32)..(1534)
<220> FEATURE:
<221> NAME/KEY: sig_peptide
<222> LOCATION: (32)..(87)
<220> FEATURE:
<221> NAME/KEY: misc_feature
<222> LOCATION: (800)..(1534)
<223> OTHER INFORMATION: Murine RANKL/TRANCE extracellular region,
      including stalk
<300> PUBLICATION INFORMATION:
<301> AUTHORS: Motwani M
<302> TITLE: Mouse surfactant protein-D. cDNA cloning,
      characterization, and gene localization to chromosome 14.
<303> JOURNAL: Journal of Immunology
<304> VOLUME: 155
<305> ISSUE: 12
<306> PAGES: 5671-5677
<307> DATE: 1995
<313> RELEVANT RESIDUES: (31)..(799)
<300> PUBLICATION INFORMATION:
<301> AUTHORS: Anderson, DM
<302> TITLE: A homologue of the TNF receptor and its ligand enhance
      T-cell growth and dendritic-cell function.
<303> JOURNAL: Nature
<304> VOLUME: 390
<305> ISSUE: 6656
<306> PAGES: 175-179
```

<307> DATE: 1997

<313> RELEVANT RESIDUES: (800)..(1534)

<400> SEQUENCE: 3

```
gctagcgaat tccaccagga agcaatctga c atg ctg ccc ttt ctc tcc atg        52
                                   Met Leu Pro Phe Leu Ser Met
                                    1               5 ctt gtc ttg ctt gta cag ccc ctg gga aat ctg gga gca gaa atg aag      100
Leu Val Leu Leu Val Gln Pro Leu Gly Asn Leu Gly Ala Glu Met Lys
            10                  15                  20 agc ctc tcg cag aga tca gta ccc aac acc tgc acc cta gtc atg tgt      148
Ser Leu Ser Gln Arg Ser Val Pro Asn Thr Cys Thr Leu Val Met Cys
 25                  30                  35 agc cca aca gag aat ggc ctg cct ggt cgt gat gga cgg gat ggg aga      196
Ser Pro Thr Glu Asn Gly Leu Pro Gly Arg Asp Gly Arg Asp Gly Arg
 40                  45                  50                  55 gaa ggt cca cgg ggt gag aag ggt gat cca ggt ttg cca gga cct atg      244
Glu Gly Pro Arg Gly Glu Lys Gly Asp Pro Gly Leu Pro Gly Pro Met
                 60                  65                  70 ggg ctc tca ggg ttg cag ggc cct aca ggt cca gtt gga ccc aaa gga      292
Gly Leu Ser Gly Leu Gln Gly Pro Thr Gly Pro Val Gly Pro Lys Gly
            75                  80                  85 gag aat ggc tct gct ggc gaa cct gga cca aag gga gaa cgt gga cta      340
Glu Asn Gly Ser Ala Gly Glu Pro Gly Pro Lys Gly Glu Arg Gly Leu
 90                  95                 100 agt gga cct cca gga ctt cca ggt att cct ggt cca gct ggg aaa gaa      388
Ser Gly Pro Pro Gly Leu Pro Gly Ile Pro Gly Pro Ala Gly Lys Glu
        105                 110                 115 ggt ccc tct ggg aag cag ggg aac ata gga cct caa ggc aaa cca ggt      436
Gly Pro Ser Gly Lys Gln Gly Asn Ile Gly Pro Gln Gly Lys Pro Gly
120                 125                 130                 135 cct aaa gga gag gct ggg ccc aaa gga gaa gta ggt gct cct ggc atg      484
Pro Lys Gly Glu Ala Gly Pro Lys Gly Glu Val Gly Ala Pro Gly Met
                140                 145                 150 caa gga tct aca ggg gca aaa ggc tcc aca ggc ccc aag gga gaa aga      532
Gln Gly Ser Thr Gly Ala Lys Gly Ser Thr Gly Pro Lys Gly Glu Arg
            155                 160                 165 ggt gcc cct ggt gtg caa gga gcc cca ggg aat gct gga gca gca gga      580
Gly Ala Pro Gly Val Gln Gly Ala Pro Gly Asn Ala Gly Ala Ala Gly
        170                 175                 180 cct gcc gga cct gcc ggt cca cag gga gct cca ggt tcc agg ggg ccc      628
Pro Ala Gly Pro Ala Gly Pro Gln Gly Ala Pro Gly Ser Arg Gly Pro
185                 190                 195 cca gga ctc aag ggg gac aga ggt gtt cct gga gac aga gga atc aaa      676
Pro Gly Leu Lys Gly Asp Arg Gly Val Pro Gly Asp Arg Gly Ile Lys
200                 205                 210                 215 ggt gaa agc ggg ctt cca gac agt gct gct ctg agg cag cag atg gag      724
Gly Glu Ser Gly Leu Pro Asp Ser Ala Ala Leu Arg Gln Gln Met Glu
                220                 225                 230 gcc tta aaa gga aaa cta cag cgt cta gag gtt gcc ttc tcc cac tat      772
Ala Leu Lys Gly Lys Leu Gln Arg Leu Glu Val Ala Phe Ser His Tyr
            235                 240                 245 cag aaa gct gca ttg ttc cct gat gga cga gcg cag atg gat cct aac      820
Gln Lys Ala Ala Leu Phe Pro Asp Gly Arg Ala Gln Met Asp Pro Asn
        250                 255                 260 aga ata tca gaa gac agc act cac tgc ttt tat aga atc ctg aga ctc      868
Arg Ile Ser Glu Asp Ser Thr His Cys Phe Tyr Arg Ile Leu Arg Leu
265                 270                 275 cat gaa aac gca ggt ttg cag gac tcg act ctg gag agt gaa gac aca      916
His Glu Asn Ala Gly Leu Gln Asp Ser Thr Leu Glu Ser Glu Asp Thr
```

-continued

```
              280                 285                 290                 295
cta cct gac tcc tgc agg agg atg aaa caa gcc ttt cag ggg gcc gtg         964
Leu Pro Asp Ser Cys Arg Arg Met Lys Gln Ala Phe Gln Gly Ala Val
                    300                 305                 310 cag aag gaa ctg caa cac att gtg ggg cca cag cgc ttc tca gga gct        1012
Gln Lys Glu Leu Gln His Ile Val Gly Pro Gln Arg Phe Ser Gly Ala
            315                 320                 325 cca gct atg atg gaa ggc tca tgg ttg gat gtg gcc cag cga ggc aag        1060
Pro Ala Met Met Glu Gly Ser Trp Leu Asp Val Ala Gln Arg Gly Lys
        330                 335                 340 cct gag gcc cag cca ttt gca cac ctc acc atc aat gct gcc agc atc        1108
Pro Glu Ala Gln Pro Phe Ala His Leu Thr Ile Asn Ala Ala Ser Ile
    345                 350                 355 cca tcg ggt tcc cat aaa gtc act ctg tcc tct tgg tac cac gat cga        1156
Pro Ser Gly Ser His Lys Val Thr Leu Ser Ser Trp Tyr His Asp Arg
360                 365                 370                 375 ggc tgg gcc aag atc tct aac atg acg tta agc aac gga aaa cta agg        1204
Gly Trp Ala Lys Ile Ser Asn Met Thr Leu Ser Asn Gly Lys Leu Arg
                    380                 385                 390 gtt aac caa gat ggc ttc tat tac ctg tac gcc aac att tgc ttt cgg        1252
Val Asn Gln Asp Gly Phe Tyr Tyr Leu Tyr Ala Asn Ile Cys Phe Arg
            395                 400                 405 cat cat gaa aca tcg gga agc gta cct aca gac tat ctt cag ctg atg        1300
His His Glu Thr Ser Gly Ser Val Pro Thr Asp Tyr Leu Gln Leu Met
        410                 415                 420 gtg tat gtc gtt aaa acc agc atc aaa atc cca agt tct cat aac ctg        1348
Val Tyr Val Val Lys Thr Ser Ile Lys Ile Pro Ser Ser His Asn Leu
    425                 430                 435 atg aaa gga ggg agc acg aaa aac tgg tcg ggc aat tct gaa ttc cac        1396
Met Lys Gly Gly Ser Thr Lys Asn Trp Ser Gly Asn Ser Glu Phe His
440                 445                 450                 455 ttt tat tcc ata aat gtt ggg gga ttt ttc aag ctc cga gct ggt gaa        1444
Phe Tyr Ser Ile Asn Val Gly Gly Phe Phe Lys Leu Arg Ala Gly Glu
                    460                 465                 470 gaa att agc att cag gtg tcc aac cct tcc ctg ctg gat ccg gat caa        1492
Glu Ile Ser Ile Gln Val Ser Asn Pro Ser Leu Leu Asp Pro Asp Gln
            475                 480                 485 gat gcg acg tac ttt ggg gct ttc aaa gtt cag gac ata gac                1534
Asp Ala Thr Tyr Phe Gly Ala Phe Lys Val Gln Asp Ile Asp
        490                 495                 500 tgagactcat ttcgtggaac attagcggcc gctaaactat                            1574
```

<210> SEQ ID NO 4
<211> LENGTH: 501
<212> TYPE: PRT
<213> ORGANISM: Artificial Sequence
<220> FEATURE:
<223> OTHER INFORMATION: Synthetic Construct

<400> SEQUENCE: 4

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
            35                  40                  45

Arg Asp Gly Arg Asp Gly Arg Glu Gly Pro Arg Gly Glu Lys Gly Asp
        50                  55                  60

Pro Gly Leu Pro Gly Pro Met Gly Leu Ser Gly Leu Gln Gly Pro Thr
```

```
                65                  70                  75                  80
Gly Pro Val Gly Pro Lys Gly Glu Asn Gly Ser Ala Gly Glu Pro Gly
                    85                  90                  95
Pro Lys Gly Glu Arg Gly Leu Ser Gly Pro Gly Leu Pro Gly Ile
                100                 105                 110
Pro Gly Pro Ala Gly Lys Glu Gly Pro Ser Gly Lys Gln Gly Asn Ile
                115                 120                 125
Gly Pro Gln Gly Lys Pro Gly Pro Lys Gly Glu Ala Gly Pro Lys Gly
                130                 135                 140
Glu Val Gly Ala Pro Gly Met Gln Gly Ser Thr Gly Ala Lys Gly Ser
145                 150                 155                 160
Thr Gly Pro Lys Gly Glu Arg Gly Ala Pro Gly Val Gln Gly Ala Pro
                    165                 170                 175
Gly Asn Ala Gly Ala Ala Gly Pro Ala Gly Pro Ala Gly Pro Gln Gly
                180                 185                 190
Ala Pro Gly Ser Arg Gly Pro Pro Gly Leu Lys Gly Asp Arg Gly Val
                195                 200                 205
Pro Gly Asp Arg Gly Ile Lys Gly Glu Ser Gly Leu Pro Asp Ser Ala
210                 215                 220
Ala Leu Arg Gln Gln Met Glu Ala Leu Lys Gly Lys Leu Gln Arg Leu
225                 230                 235                 240
Glu Val Ala Phe Ser His Tyr Gln Lys Ala Ala Leu Phe Pro Asp Gly
                    245                 250                 255
Arg Ala Gln Met Asp Pro Asn Arg Ile Ser Glu Asp Ser Thr His Cys
                260                 265                 270
Phe Tyr Arg Ile Leu Arg Leu His Glu Asn Ala Gly Leu Gln Asp Ser
                275                 280                 285
Thr Leu Glu Ser Glu Asp Thr Leu Pro Asp Ser Cys Arg Arg Met Lys
                290                 295                 300
Gln Ala Phe Gln Gly Ala Val Gln Lys Glu Leu Gln His Ile Val Gly
305                 310                 315                 320
Pro Gln Arg Phe Ser Gly Ala Pro Ala Met Met Glu Gly Ser Trp Leu
                    325                 330                 335
Asp Val Ala Gln Arg Gly Lys Pro Glu Ala Gln Pro Phe Ala His Leu
                340                 345                 350
Thr Ile Asn Ala Ala Ser Ile Pro Ser Gly Ser His Lys Val Thr Leu
                355                 360                 365
Ser Ser Trp Tyr His Asp Arg Gly Trp Ala Lys Ile Ser Asn Met Thr
370                 375                 380
Leu Ser Asn Gly Lys Leu Arg Val Asn Gln Asp Gly Phe Tyr Tyr Leu
385                 390                 395                 400
Tyr Ala Asn Ile Cys Phe Arg His His Glu Thr Ser Gly Ser Val Pro
                    405                 410                 415
Thr Asp Tyr Leu Gln Leu Met Val Tyr Val Val Lys Thr Ser Ile Lys
                420                 425                 430
Ile Pro Ser Ser His Asn Leu Met Lys Gly Gly Ser Thr Lys Asn Trp
                435                 440                 445
Ser Gly Asn Ser Glu Phe His Phe Tyr Ser Ile Asn Val Gly Gly Phe
                450                 455                 460
Phe Lys Leu Arg Ala Gly Glu Glu Ile Ser Ile Gln Val Ser Asn Pro
465                 470                 475                 480
Ser Leu Leu Asp Pro Asp Gln Asp Ala Thr Tyr Phe Gly Ala Phe Lys
                    485                 490                 495
```

Val Gln Asp Ile Asp
        500

<210> SEQ ID NO 5
<211> LENGTH: 1477
<212> TYPE: DNA
<213> ORGANISM: Artificial Sequence
<220> FEATURE:
<223> OTHER INFORMATION: Murine surfactant protein D (except CRD) fused
      to the extracellular domain of murine CD40 ligand
<220> FEATURE:
<221> NAME/KEY: 5'UTR
<222> LOCATION: (7)..(31)
<223> OTHER INFORMATION: 5'UTR from rat surfactant protein D
<220> FEATURE:
<221> NAME/KEY: CDS
<222> LOCATION: (32)..(1441)
<220> FEATURE:
<221> NAME/KEY: sig_peptide
<222> LOCATION: (32)..(87)
<223> OTHER INFORMATION: Signal peptide from murine surfactant protein D
<220> FEATURE:
<221> NAME/KEY: misc_feature
<222> LOCATION: (88)..(799)
<220> FEATURE:
<221> NAME/KEY: misc_feature
<222> LOCATION: (800)..(1441)
<300> PUBLICATION INFORMATION:
<301> AUTHORS: Motwani M
<302> TITLE: Mouse surfactant protein-D.  cDNA clonings,
       characterization, and gene localization to chromosome 14.
<303> JOURNAL: Nature
<304> VOLUME: 357
<305> ISSUE: 6373
<306> PAGES: 80 TO 82
<307> DATE: 1992-05-07
<313> RELEVANT RESIDUES: (801)..(1441)
<300> PUBLICATION INFORMATION:
<301> AUTHORS: Armitage RJ
<302> TITLE: Molecular and biological characterization of a murine
       ligand for CD40.
<303> JOURNAL: Nature
<304> VOLUME: 357
<305> ISSUE: 6373
<306> PAGES: 80 TO 82
<307> DATE: 1992-05-07
<313> RELEVANT RESIDUES: (801)..(1441)

<400> SEQUENCE: 5
gctagcgaat tccaccagga agcaatctga c atg ctg ccc ttt ctc tcc atg         52
                                   Met Leu Pro Phe Leu Ser Met
                                    1               5 ctt gtc ttg ctt gta cag ccc ctg gga aat ctg gga gca gaa atg aag       100
Leu Val Leu Leu Val Gln Pro Leu Gly Asn Leu Gly Ala Glu Met Lys
         10                  15                  20 agc ctc tcg cag aga tca gta ccc aac acc tgc acc cta gtc atg tgt       148
Ser Leu Ser Gln Arg Ser Val Pro Asn Thr Cys Thr Leu Val Met Cys
 25                  30                  35 agc cca aca gag aat ggc ctg cct ggt cgt gat gga cgg gat ggg aga       196
Ser Pro Thr Glu Asn Gly Leu Pro Gly Arg Asp Gly Arg Asp Gly Arg
 40                  45                  50                  55 gaa ggt cca cgg ggt gag aag ggt gat cca ggt ttg cca gga cct atg       244
Glu Gly Pro Arg Gly Glu Lys Gly Asp Pro Gly Leu Pro Gly Pro Met
                 60                  65                  70 ggg ctc tca ggg ttg cag ggc cct aca ggt cca gtt gga ccc aaa gga       292
Gly Leu Ser Gly Leu Gln Gly Pro Thr Gly Pro Val Gly Pro Lys Gly
             75                  80                  85 gag aat ggc tct gct ggc gaa cct gga cca aag gga gaa cgt gga cta       340
Glu Asn Gly Ser Ala Gly Glu Pro Gly Pro Lys Gly Glu Arg Gly Leu
         90                  95                 100

-continued

```
agt gga cct cca gga ctt cca ggt att cct ggt cca gct ggg aaa gaa      388
Ser Gly Pro Pro Gly Leu Pro Gly Ile Pro Gly Pro Ala Gly Lys Glu
    105                 110                 115 ggt ccc tct ggg aag cag ggg aac ata gga cct caa ggc aaa cca ggt      436
Gly Pro Ser Gly Lys Gln Gly Asn Ile Gly Pro Gln Gly Lys Pro Gly
120                 125                 130                 135 cct aaa gga gag gct ggg ccc aaa gga gaa gta ggt gct cct ggc atg      484
Pro Lys Gly Glu Ala Gly Pro Lys Gly Glu Val Gly Ala Pro Gly Met
                140                 145                 150 caa gga tct aca ggg gca aaa ggc tcc aca ggc ccc aag gga gaa aga      532
Gln Gly Ser Thr Gly Ala Lys Gly Ser Thr Gly Pro Lys Gly Glu Arg
            155                 160                 165 ggt gcc cct ggt gtg caa gga gcc cca ggg aat gct gga gca gca gga      580
Gly Ala Pro Gly Val Gln Gly Ala Pro Gly Asn Ala Gly Ala Ala Gly
        170                 175                 180 cct gcc gga cct gcc ggt cca cag gga gct cca ggt tcc agg ggg ccc      628
Pro Ala Gly Pro Ala Gly Pro Gln Gly Ala Pro Gly Ser Arg Gly Pro
    185                 190                 195 cca gga ctc aag ggg gac aga ggt gtt cct gga gac aga gga atc aaa      676
Pro Gly Leu Lys Gly Asp Arg Gly Val Pro Gly Asp Arg Gly Ile Lys
200                 205                 210                 215 ggt gaa agc ggg ctt cca gac agt gct gct ctg agg cag cag atg gag      724
Gly Glu Ser Gly Leu Pro Asp Ser Ala Ala Leu Arg Gln Gln Met Glu
                220                 225                 230 gcc tta aaa gga aaa cta cag cgt cta gag gtt gcc ttc tcc cac tat      772
Ala Leu Lys Gly Lys Leu Gln Arg Leu Glu Val Ala Phe Ser His Tyr
            235                 240                 245 cag aaa gct gca ttg ttc cct gat ggc cat aga aga ttg gat aag gtc      820
Gln Lys Ala Ala Leu Phe Pro Asp Gly His Arg Arg Leu Asp Lys Val
        250                 255                 260 gaa gag gaa gta aac ctt cat gaa gat ttt gta ttc ata aaa aag cta      868
Glu Glu Glu Val Asn Leu His Glu Asp Phe Val Phe Ile Lys Lys Leu
    265                 270                 275 aag aga tgc aac aaa gga gaa gga tct tta tcc ttg ctg aac tgt gag      916
Lys Arg Cys Asn Lys Gly Glu Gly Ser Leu Ser Leu Leu Asn Cys Glu
280                 285                 290                 295 gag atg aga agg caa ttt gaa gac ctt gtc aag gat ata acg tta aac      964
Glu Met Arg Arg Gln Phe Glu Asp Leu Val Lys Asp Ile Thr Leu Asn
                300                 305                 310 aaa gaa gag aaa aaa gaa aac agc ttt gaa atg caa aga ggt gat gag     1012
Lys Glu Glu Lys Lys Glu Asn Ser Phe Glu Met Gln Arg Gly Asp Glu
            315                 320                 325 gat cct caa att gca gca cac gtt gta agc gaa gcc aac agt aat gca     1060
Asp Pro Gln Ile Ala Ala His Val Val Ser Glu Ala Asn Ser Asn Ala
        330                 335                 340 gca tcc gtt cta cag tgg gcc aag aaa gga tat tat acc atg aaa agc     1108
Ala Ser Val Leu Gln Trp Ala Lys Lys Gly Tyr Tyr Thr Met Lys Ser
    345                 350                 355 aac ttg gta atg ctt gaa aat ggg aaa cag ctg acg gtt aaa aga gaa     1156
Asn Leu Val Met Leu Glu Asn Gly Lys Gln Leu Thr Val Lys Arg Glu
360                 365                 370                 375 gga ctc tat tat gtc tac act caa gtc acc ttc tgc tct aat cgg gag     1204
Gly Leu Tyr Tyr Val Tyr Thr Gln Val Thr Phe Cys Ser Asn Arg Glu
                380                 385                 390 cct tcg agt caa cgc cca ttc atc gtc ggc ctc tgg ctg aag ccc agc     1252
Pro Ser Ser Gln Arg Pro Phe Ile Val Gly Leu Trp Leu Lys Pro Ser
            395                 400                 405 att gga tct gag aga atc tta ctc aag gcg gca aat acc cac agt tcc     1300
Ile Gly Ser Glu Arg Ile Leu Leu Lys Ala Ala Asn Thr His Ser Ser
```

-continued

```
                   410                 415                 420
tcc cag ctt tgc gag cag cag tct gtt cac ttg ggc gga gtg ttt gaa    1348
Ser Gln Leu Cys Glu Gln Gln Ser Val His Leu Gly Gly Val Phe Glu
    425                 430                 435 tta caa gct ggt gct tct gtg ttt gtc aac gtg act gaa gca agc caa    1396
Leu Gln Ala Gly Ala Ser Val Phe Val Asn Val Thr Glu Ala Ser Gln
440                 445                 450                 455 gtg atc cac aga gtt ggc ttc tca tct ttt ggc tta ctc aaa ctc        1441
Val Ile His Arg Val Gly Phe Ser Ser Phe Gly Leu Leu Lys Leu
                460                 465                 470 tgaacagtgc gctgtcctag gctgcagcag ggtacc                            1477
```

<210> SEQ ID NO 6
<211> LENGTH: 470
<212> TYPE: PRT
<213> ORGANISM: Artificial Sequence
<220> FEATURE:
<223> OTHER INFORMATION: Synthetic Construct

<400> SEQUENCE: 6

```
Met Leu Pro Phe Leu Ser Met Leu Val Leu Val Gln Pro Leu Gly
1               5                   10                  15

Asn Leu Gly Ala Glu Met Lys Ser Leu Ser Gln Arg Ser Val Pro Asn
                20                  25                  30

Thr Cys Thr Leu Val Met Cys Ser Pro Thr Glu Asn Gly Leu Pro Gly
            35                  40                  45

Arg Asp Gly Arg Asp Gly Arg Glu Gly Pro Arg Gly Glu Lys Gly Asp
        50                  55                  60

Pro Gly Leu Pro Gly Pro Met Gly Leu Ser Leu Gln Gly Pro Thr
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Ser Gly Pro Pro Gly Leu Pro Gly Ile
            100                 105                 110

Pro Gly Pro Ala Gly Lys Glu Gly Pro Ser Gly Lys Gln Gly Asn Ile
        115                 120                 125

Gly Pro Gln Gly Lys Pro Gly Pro Lys Gly Glu Ala Gly Pro Lys Gly
    130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
        195                 200                 205

Pro Gly Asp Arg Gly Ile Lys Gly Glu Ser Gly Leu Pro Asp Ser Ala
    210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Val Glu Glu Val Asn Leu His Glu Asp
            260                 265                 270

Phe Val Phe Ile Lys Lys Leu Lys Arg Cys Asn Lys Gly Glu Gly Ser
        275                 280                 285
```

-continued

```
Leu Ser Leu Leu Asn Cys Glu Glu Met Arg Arg Gln Phe Glu Asp Leu
        290                 295                 300
Val Lys Asp Ile Thr Leu Asn Lys Glu Glu Lys Lys Glu Asn Ser Phe
305                 310                 315                 320
Glu Met Gln Arg Gly Asp Glu Asp Pro Gln Ile Ala Ala His Val Val
                325                 330                 335
Ser Glu Ala Asn Ser Asn Ala Ala Ser Val Leu Gln Trp Ala Lys Lys
            340                 345                 350
Gly Tyr Tyr Thr Met Lys Ser Asn Leu Val Met Leu Glu Asn Gly Lys
        355                 360                 365
Gln Leu Thr Val Lys Arg Glu Gly Leu Tyr Tyr Val Tyr Thr Gln Val
    370                 375                 380
Thr Phe Cys Ser Asn Arg Glu Pro Ser Ser Gln Arg Pro Phe Ile Val
385                 390                 395                 400
Gly Leu Trp Leu Lys Pro Ser Ile Gly Ser Glu Arg Ile Leu Leu Lys
                405                 410                 415
Ala Ala Asn Thr His Ser Ser Ser Gln Leu Cys Glu Gln Gln Ser Val
            420                 425                 430
His Leu Gly Gly Val Phe Glu Leu Gln Ala Gly Ala Ser Val Phe Val
        435                 440                 445
Asn Val Thr Glu Ala Ser Gln Val Ile His Arg Val Gly Phe Ser Ser
    450                 455                 460
Phe Gly Leu Leu Lys Leu
465                 470

<210> SEQ ID NO 7
<211> LENGTH: 27
<212> TYPE: DNA
<213> ORGANISM: Artificial sequence
<220> FEATURE:
<223> OTHER INFORMATION: PCR primer

<400> SEQUENCE: 7
ctgacatgct gcccttctc tccatgc                                    27

<210> SEQ ID NO 8
<211> LENGTH: 29
<212> TYPE: DNA
<213> ORGANISM: Artificial sequence
<220> FEATURE:
<223> OTHER INFORMATION: PCR primer

<400> SEQUENCE: 8
ggaggccagc tgtcctccag cctgtttgc                                 29

<210> SEQ ID NO 9
<211> LENGTH: 56
<212> TYPE: DNA
<213> ORGANISM: Artificial sequence
<220> FEATURE:
<223> OTHER INFORMATION: PCR primer

<400> SEQUENCE: 9
ggggctagcg aattccacca ggaagcaatc tgacatgctg cccttctct ccatgc    56

<210> SEQ ID NO 10
<211> LENGTH: 48
<212> TYPE: DNA
<213> ORGANISM: Artificial sequence
<220> FEATURE:
```

-continued

<223> OTHER INFORMATION: PCR primer

<400> SEQUENCE: 10
tctatcttgt ccaaccttct atggccatca gggaacaatg cagctttc          48

<210> SEQ ID NO 11
<211> LENGTH: 49
<212> TYPE: DNA
<213> ORGANISM: Artificial sequence
<220> FEATURE:
<223> OTHER INFORMATION: PCR primer

<400> SEQUENCE: 11
aaagctgcat tgttccctga tggccataga aggttggaca agatagaag          49

<210> SEQ ID NO 12
<211> LENGTH: 41
<212> TYPE: DNA
<213> ORGANISM: Artificial sequence
<220> FEATURE:
<223> OTHER INFORMATION: PCR primer

<400> SEQUENCE: 12
gggctcgagg taccagttct acatgccttg gagtgtataa t          41

<210> SEQ ID NO 13
<211> LENGTH: 50
<212> TYPE: DNA
<213> ORGANISM: Artificial sequence
<220> FEATURE:
<223> OTHER INFORMATION: PCR primer

<400> SEQUENCE: 13
gaaagctgca ttgttccctg atggccatag aagattggat aaggtcgaag          50

<210> SEQ ID NO 14
<211> LENGTH: 50
<212> TYPE: DNA
<213> ORGANISM: Artificial sequence
<220> FEATURE:
<223> OTHER INFORMATION: PCR primer

<400> SEQUENCE: 14
cttcgacctt atccaatctt ctatggccat cagggaacaa tgcagctttc          50

<210> SEQ ID NO 15
<211> LENGTH: 34
<212> TYPE: DNA
<213> ORGANISM: Artificial sequence
<220> FEATURE:
<223> OTHER INFORMATION: PCR primer

<400> SEQUENCE: 15 gggggggtacc ctgctgcagc ctaggacagc gcac          34

<210> SEQ ID NO 16
<211> LENGTH: 16
<212> TYPE: PRT
<213> ORGANISM: Artificial sequence
<220> FEATURE:
<223> OTHER INFORMATION: Fusion segment of SPD and CD40L sequence region

<400> SEQUENCE: 16

Lys Ala Ala Leu Phe Pro Asp Gly His Arg Arg Leu Asp Lys Ile Glu
1               5                   10                  15

```
<210> SEQ ID NO 17
<211> LENGTH: 16
<212> TYPE: PRT
<213> ORGANISM: Artificial sequence
<220> FEATURE:
<223> OTHER INFORMATION: Fusion segment of SPD and murine CD40L sequence
      region

<400> SEQUENCE: 17

Lys Ala Ala Leu Phe Pro Asp Gly His Arg Arg Leu Asp Lys Val Glu
1               5                   10                  15

<210> SEQ ID NO 18
<211> LENGTH: 19
<212> TYPE: DNA
<213> ORGANISM: Artificial sequence
<220> FEATURE:
<223> OTHER INFORMATION: PCR primer

<400> SEQUENCE: 18
catgttcctg gccctcctc                                                  19

<210> SEQ ID NO 19
<211> LENGTH: 22
<212> TYPE: DNA
<213> ORGANISM: Artificial sequence
<220> FEATURE:
<223> OTHER INFORMATION: PCR primer

<400> SEQUENCE: 19
gtacaggctc aagagagagg gc                                              22

<210> SEQ ID NO 20
<211> LENGTH: 26
<212> TYPE: DNA
<213> ORGANISM: Artificial sequence
<220> FEATURE:
<223> OTHER INFORMATION: PCR primer

<400> SEQUENCE: 20
atactcgagc gcagatggat cctaac                                          26

<210> SEQ ID NO 21
<211> LENGTH: 38
<212> TYPE: DNA
<213> ORGANISM: Artificial sequence
<220> FEATURE:
<223> OTHER INFORMATION: PCR primer

<400> SEQUENCE: 21
ggggtttagc ggccgctaat gttccacgaa atgagttc                             38

<210> SEQ ID NO 22
<211> LENGTH: 16
<212> TYPE: PRT
<213> ORGANISM: Artificial sequence
<220> FEATURE:
<223> OTHER INFORMATION: Fusion sequence of SPD and RANKL/TRANCE
      sequence region

<400> SEQUENCE: 22

Lys Ala Ala Leu Phe Pro Asp Gly Arg Ala Gln Met Asp Pro Asn Arg
1               5                   10                  15
```